(12) United States Patent
Meads, Jr. et al.

(10) Patent No.: US 12,426,946 B2
(45) Date of Patent: Sep. 30, 2025

(54) NASAL COAGULATION SUCTION DEVICE AND METHODS

(71) Applicants: Garner B. Meads, Jr., Sandy, UT (US); Scott Anjewierden, Salt Lake City, UT (US); James B. Newton, Holladay, UT (US); Dane W. Barton, Salt Lake City, UT (US); Nathan J. Knighton, Salt Lake City, UT (US); Samuel C. Thomas, Salt Lake City, UT (US)

(72) Inventors: Garner B. Meads, Jr., Sandy, UT (US); Scott Anjewierden, Salt Lake City, UT (US); James B. Newton, Holladay, UT (US); Dane W. Barton, Salt Lake City, UT (US); Nathan J. Knighton, Salt Lake City, UT (US); Samuel C. Thomas, Salt Lake City, UT (US)

( * ) Notice: Subject to any disclaimer, the term of this patent is extended or adjusted under 35 U.S.C. 154(b) by 225 days.

(21) Appl. No.: 17/074,367

(22) Filed: Oct. 19, 2020

(65) Prior Publication Data

US 2021/0030469 A1    Feb. 4, 2021

Related U.S. Application Data

(63) Continuation of application No. 15/722,928, filed on Oct. 2, 2017, now Pat. No. 10,806,512, which is a
(Continued)

(51) Int. Cl.
*A61B 18/12*    (2006.01)
*A61B 18/14*    (2006.01)
(Continued)

(52) U.S. Cl.
CPC ....... *A61B 18/1492* (2013.01); *A61M 1/7411* (2021.05); *A61M 1/743* (2021.05);
(Continued)

(58) Field of Classification Search
CPC .......... A61B 18/1492; A61B 2018/144; A61B 2018/00595; A61B 2018/00327; A61B 2018/1467; A61B 2018/00589
See application file for complete search history.

(56) References Cited

U.S. PATENT DOCUMENTS

| 4,932,952 A | 6/1990 | Wojciechowicz, Jr. |
| 5,015,227 A | 5/1991 | Broadwin et al. |

(Continued)

OTHER PUBLICATIONS

US 8,845,579 B2, 09/2014, DeBelser et al. (withdrawn)
(Continued)

*Primary Examiner* — Daniel W Fowler
(74) *Attorney, Agent, or Firm* — HOLLAND & HART LLP

(57) ABSTRACT

A coagulation suction device having an insulation cover and first and second bipolar wires. The insulation cover has a distal end and a distal opening formed at the distal end, and a hollow cavity configured to receive a hollow suction tube. The first and second bipolar wires are encapsulated within the insulation cover and extend along the insulation cover to the distal end. The first and second bipolar wires extend distally beyond a distal-most surface of the insulation cover, and each have an exposed distal end. The exposed distal ends are bent toward each other and terminate adjacent to and spaced apart from each other.

20 Claims, 13 Drawing Sheets

Related U.S. Application Data continuation-in-part of application No. 15/083,050, filed on Mar. 28, 2016, now Pat. No. 9,775,673.

(60) Provisional application No. 62/138,579, filed on Mar. 26, 2015.

(51) Int. Cl.
| | |
|---|---|
| *A61M 1/00* | (2006.01) |
| *A61B 17/00* | (2006.01) |
| *A61B 17/24* | (2006.01) |
| *A61B 18/00* | (2006.01) |
| *A61M 25/01* | (2006.01) |

(52) U.S. Cl.
CPC ............... *A61M 1/84* (2021.05); *A61M 1/86* (2021.05); *A61B 2017/00269* (2013.01); *A61B 2017/00561* (2013.01); *A61B 2017/00734* (2013.01); *A61B 2017/00946* (2013.01); *A61B 2017/00955* (2013.01); *A61B 17/24* (2013.01); *A61B 2018/00077* (2013.01); *A61B 2018/00083* (2013.01); *A61B 2018/00327* (2013.01); *A61B 2018/00404* (2013.01); *A61B 2018/00589* (2013.01); *A61B 2018/00595* (2013.01); *A61B 18/1206* (2013.01); *A61B 2018/126* (2013.01); *A61B 2018/144* (2013.01); *A61B 2018/1467* (2013.01); *A61B 2217/005* (2013.01); *A61B 2218/007* (2013.01); *A61M 25/0152* (2013.01); *A61M 2205/0266* (2013.01); *A61M 2206/20* (2013.01); *A61M 2210/0618* (2013.01); *A61M 2210/0681* (2013.01)

(56) References Cited

U.S. PATENT DOCUMENTS

| | | | |
|---|---|---|---|
| 5,186,714 A | 2/1993 | Boudreault et al. | |
| 5,217,459 A | 6/1993 | Kamerling | |
| 5,334,193 A | 8/1994 | Nardella | |
| 5,441,498 A * | 8/1995 | Perkins | A61B 18/1442 604/35 |
| 5,617,854 A | 4/1997 | Munsif | |
| 5,989,249 A | 11/1999 | Kirwan, Jr. | |
| 6,120,500 A | 9/2000 | Bednarek et al. | |
| 6,409,728 B1 * | 6/2002 | Ehr | A61B 18/1445 606/205 |
| 6,458,126 B1 | 10/2002 | Doyle | |
| 6,669,692 B1 | 12/2003 | Nelson et al. | |
| 7,122,035 B2 | 10/2006 | Canady | |
| 8,187,272 B2 | 5/2012 | Sensenbrenner et al. | |
| 8,808,287 B2 | 8/2014 | Heard et al. | |
| 8,974,455 B2 | 3/2015 | Bacher et al. | |
| 2001/0039415 A1 | 11/2001 | Francischelli et al. | |
| 2002/0087158 A1 | 7/2002 | McGill | |
| 2003/0225403 A1 | 12/2003 | Woloszko et al. | |
| 2004/0138621 A1 * | 7/2004 | Jahns | A61B 17/3478 604/173 |
| 2007/0219551 A1 * | 9/2007 | Honour | A61B 5/6852 606/41 |
| 2008/0071262 A1 | 3/2008 | Azure | |
| 2008/0086121 A1 * | 4/2008 | Sensenbrenner | A61B 18/1482 606/50 |
| 2008/0215044 A1 | 9/2008 | Devers | |
| 2009/0228001 A1 | 9/2009 | Pacey | |
| 2009/0234354 A1 * | 9/2009 | Johnson | A61B 18/1402 606/48 |
| 2010/0114093 A1 * | 5/2010 | Mahapatra | A61M 25/0133 606/41 |
| 2011/0022048 A1 * | 1/2011 | Bacher | A61B 18/1482 606/50 |
| 2011/0178444 A1 * | 7/2011 | Slayton | A61N 5/10 601/3 |
| 2012/0116367 A1 | 5/2012 | Houser et al. | |
| 2012/0303022 A1 * | 11/2012 | Deshpande | A61B 18/1492 606/45 |
| 2013/0331830 A1 * | 12/2013 | Podhajsky | A61B 18/1445 606/29 |
| 2014/0121656 A1 * | 5/2014 | McKay | A61B 18/148 606/33 |
| 2014/0276811 A1 * | 9/2014 | Koblish | A61B 18/1492 606/47 |

OTHER PUBLICATIONS

Wormald Bipolar Forceps with Suction, Medtronic, Jan. 9, 2013 (2 pp.).
Dessi Nasal Bipolar Forceps, Medtronic, Jan. 9, 2013 (2 pp.).
Injection Gold Probe™ and Gold Probe™, Boston Scientific, available at least as early as Mar. 4, 2015 (4 pp.).
ConMed Suction Coagulators Brochure, ConMed Electrosurgery, Oct. 2010 (2 pp.).

\* cited by examiner

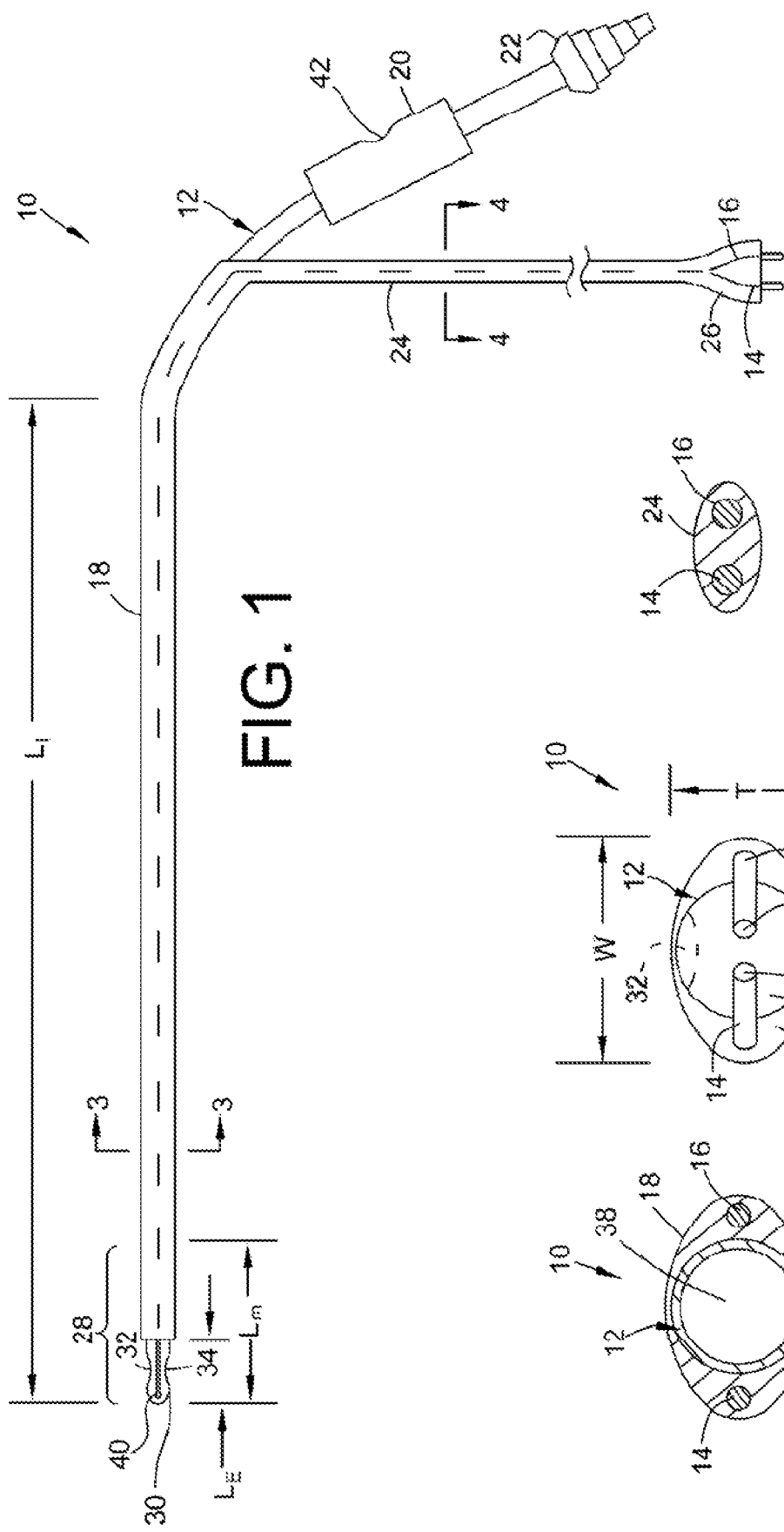

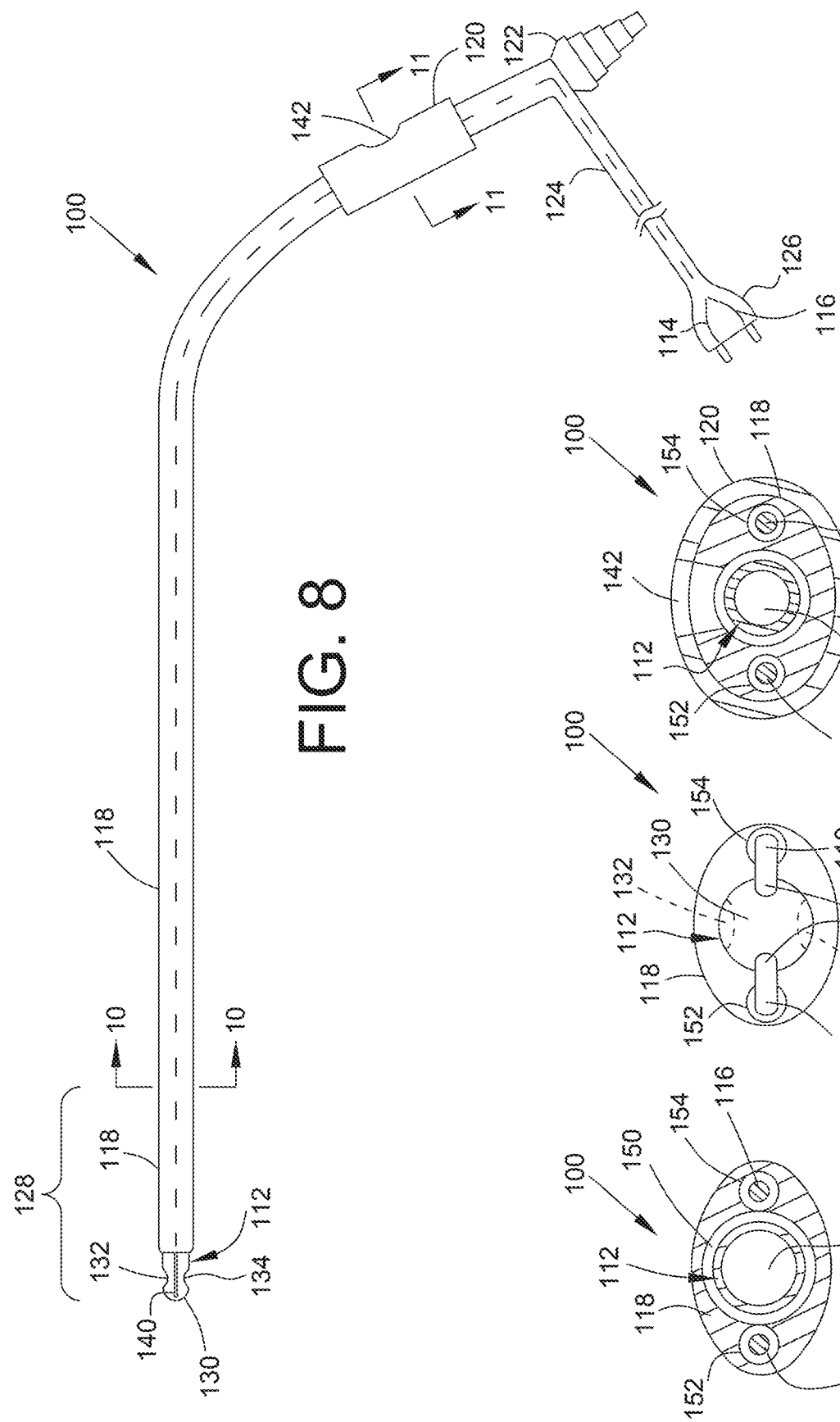

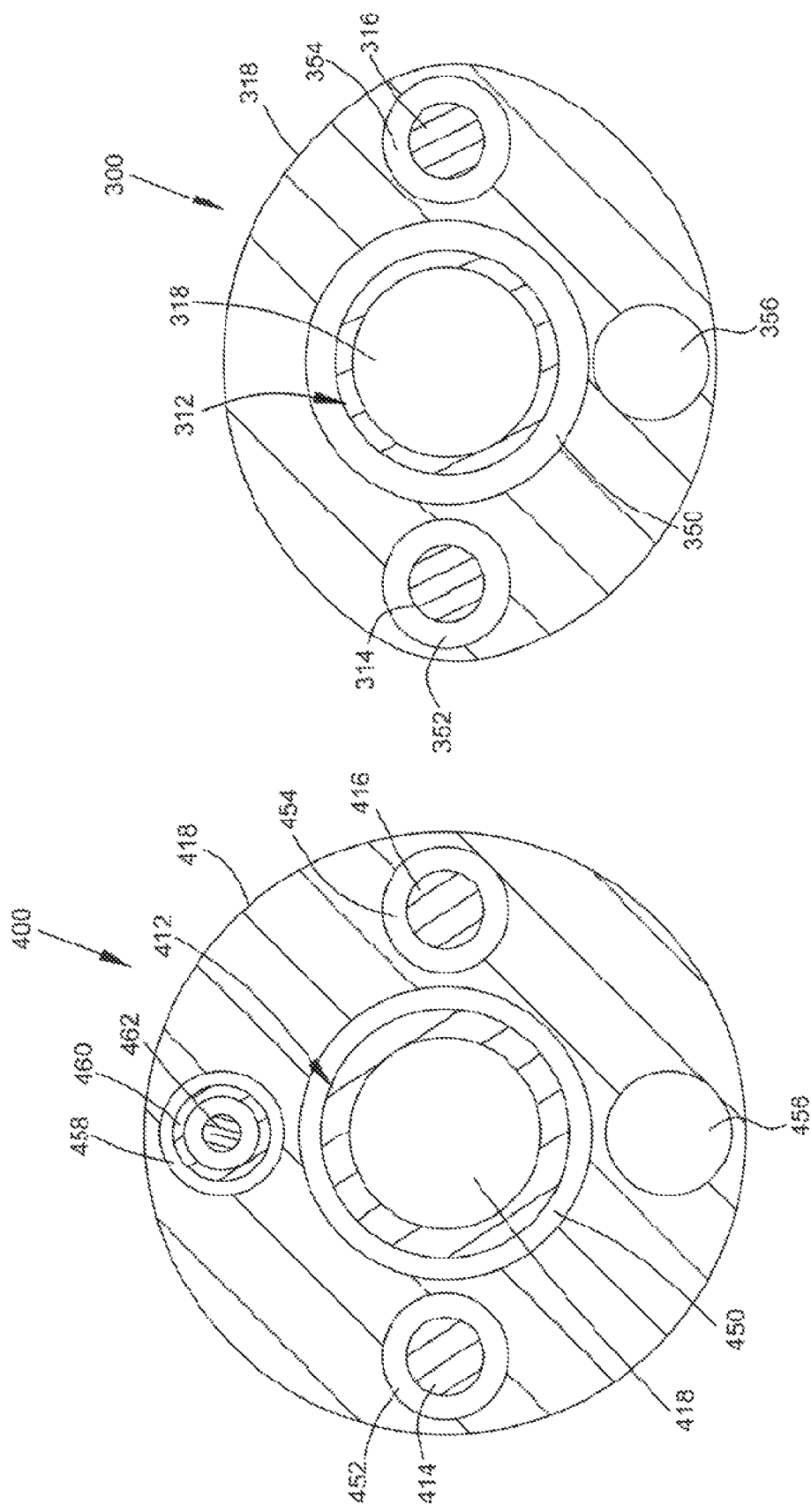

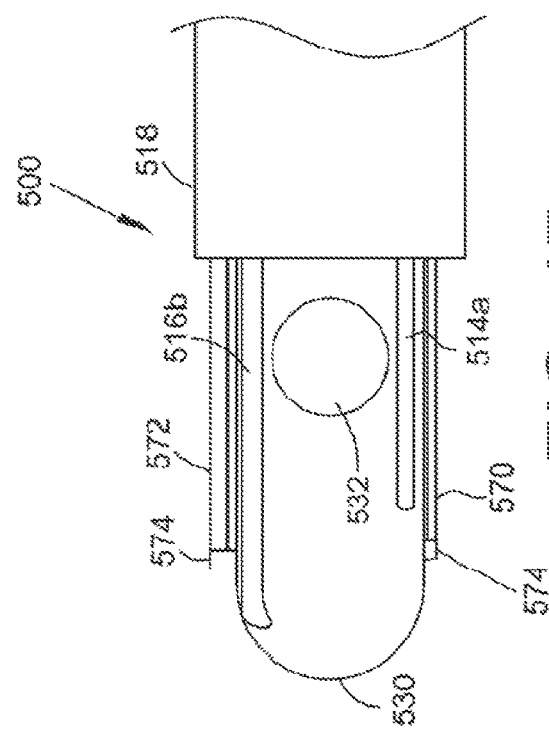
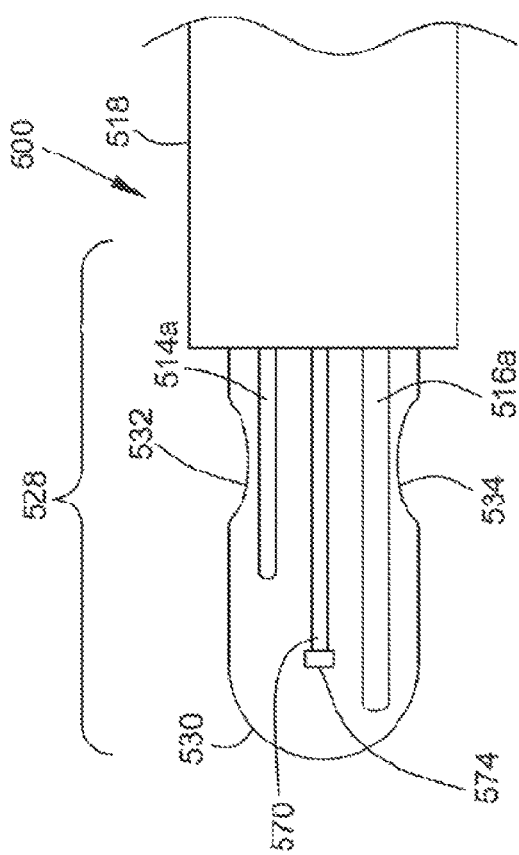
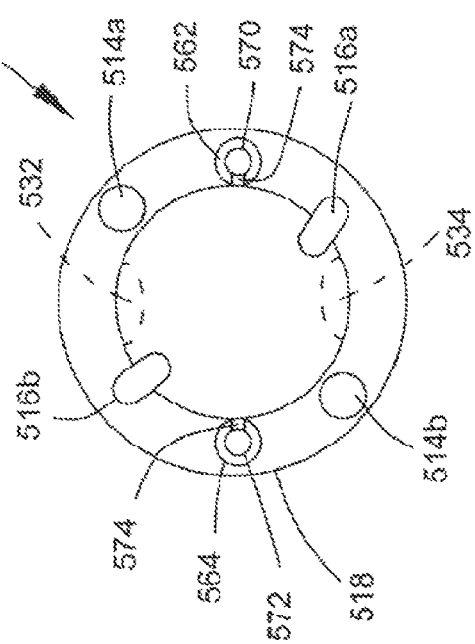

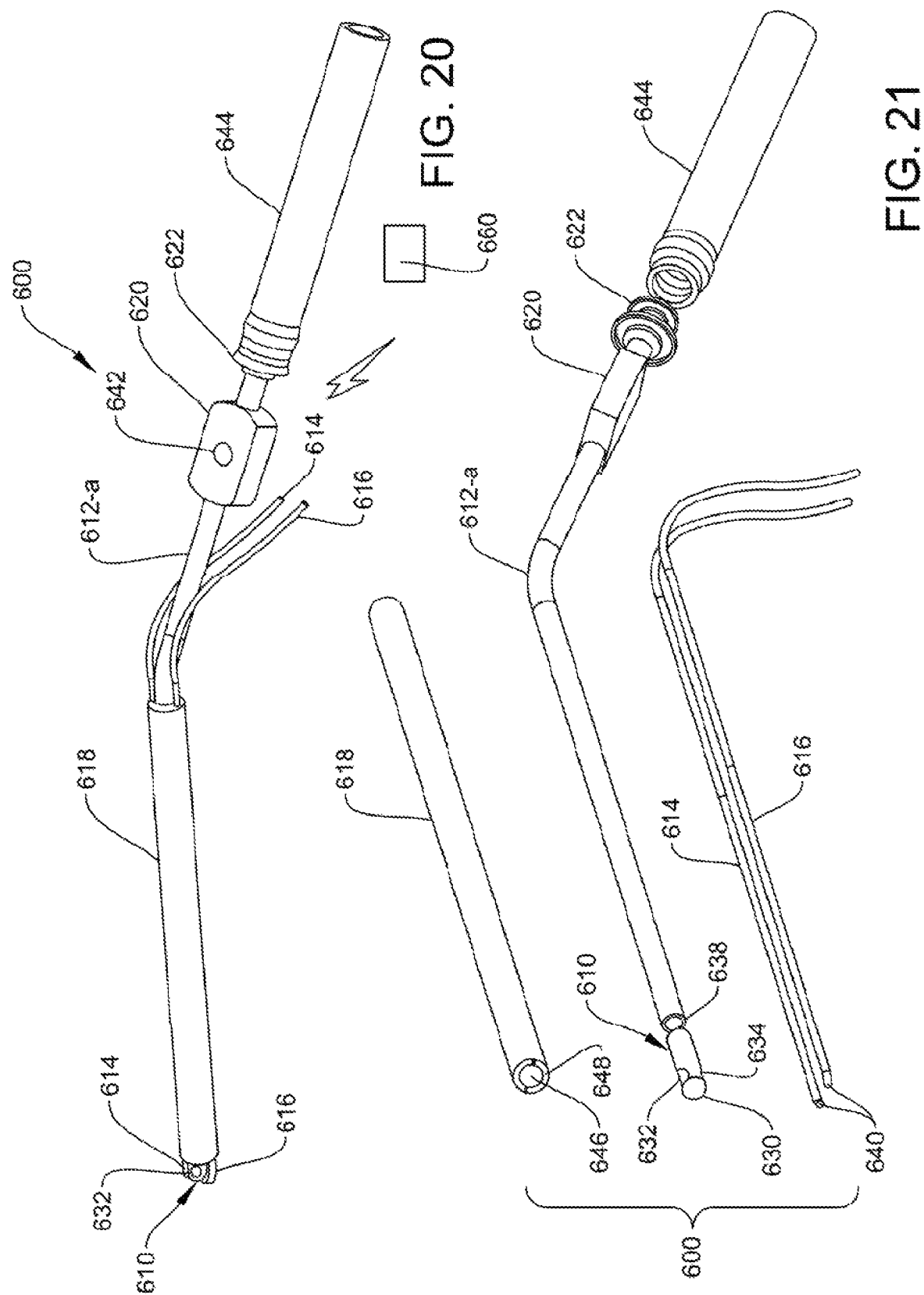

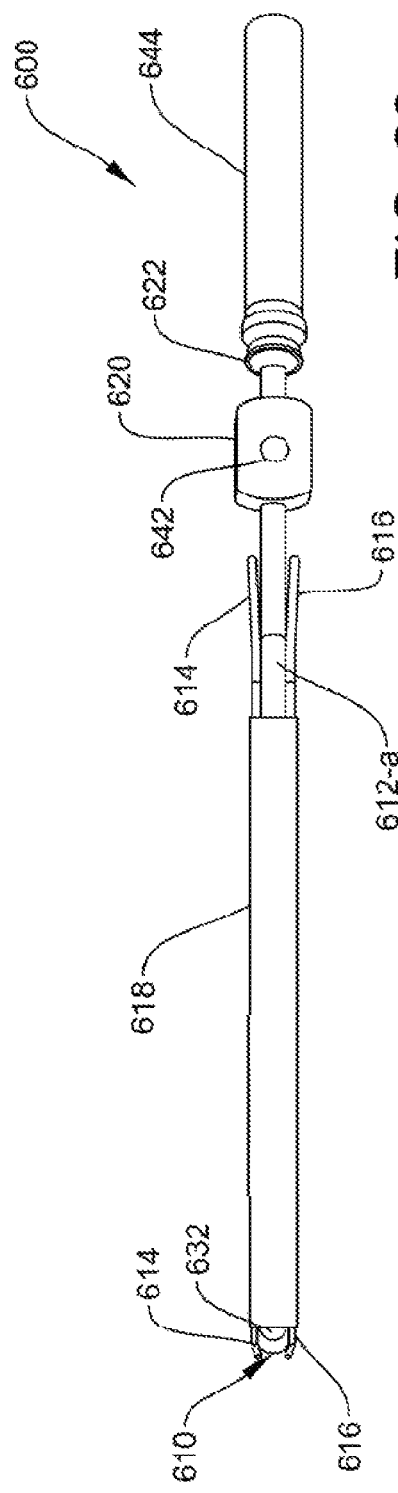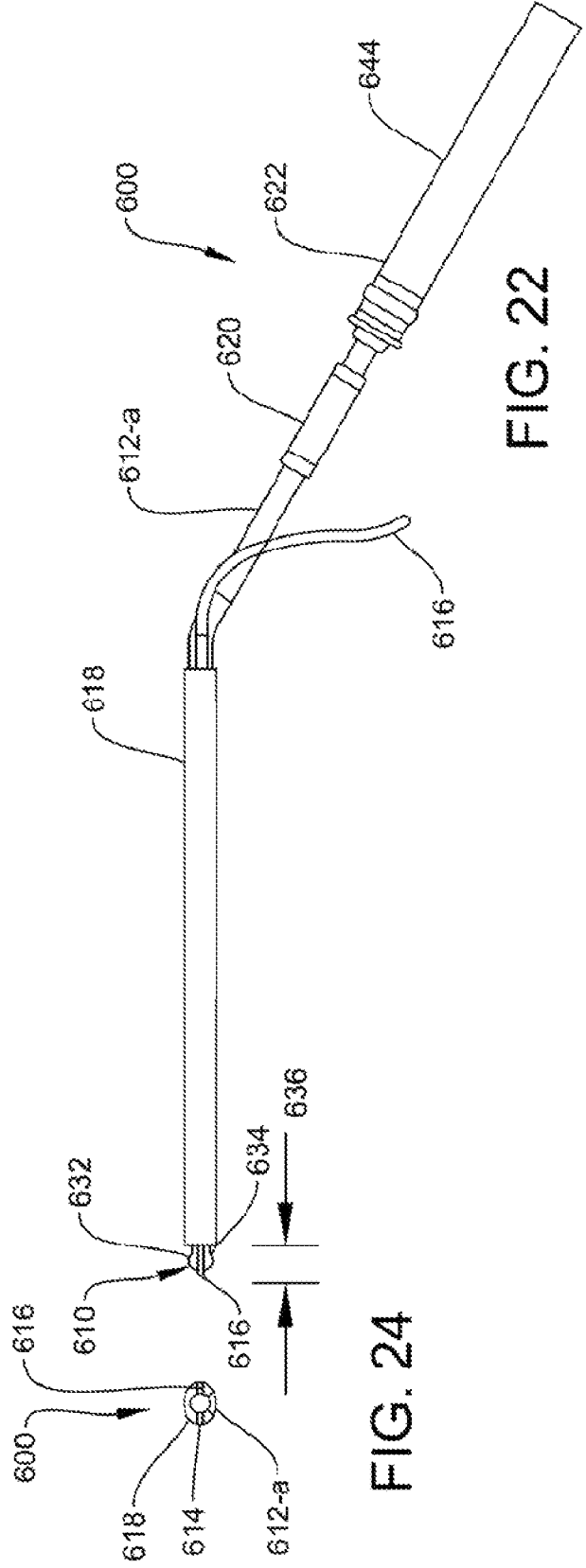

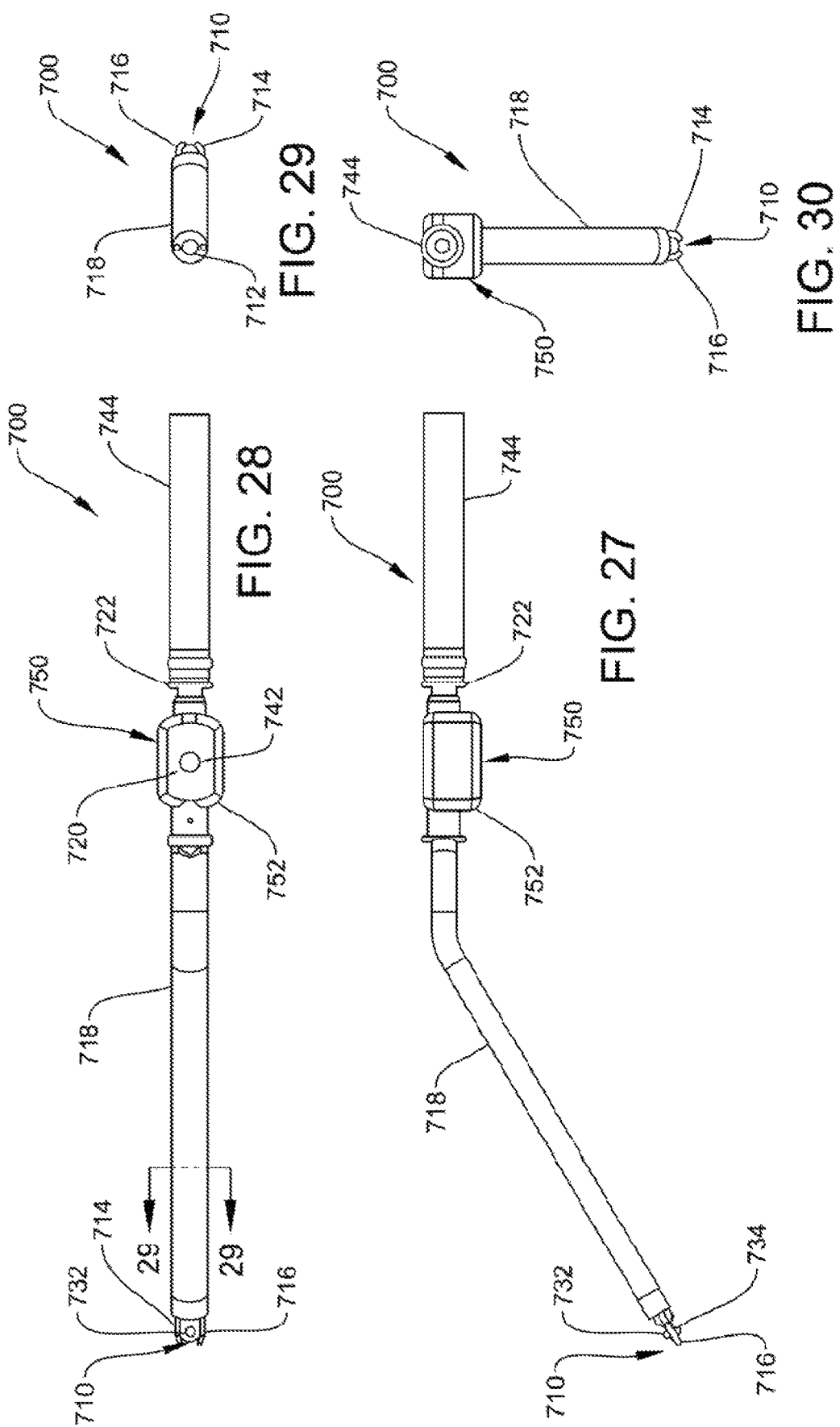

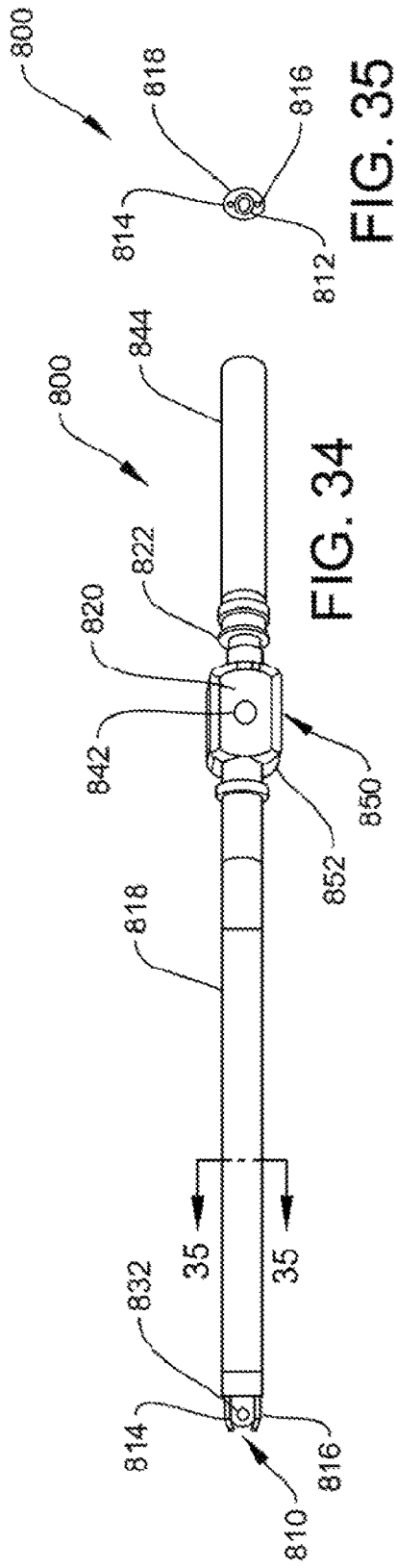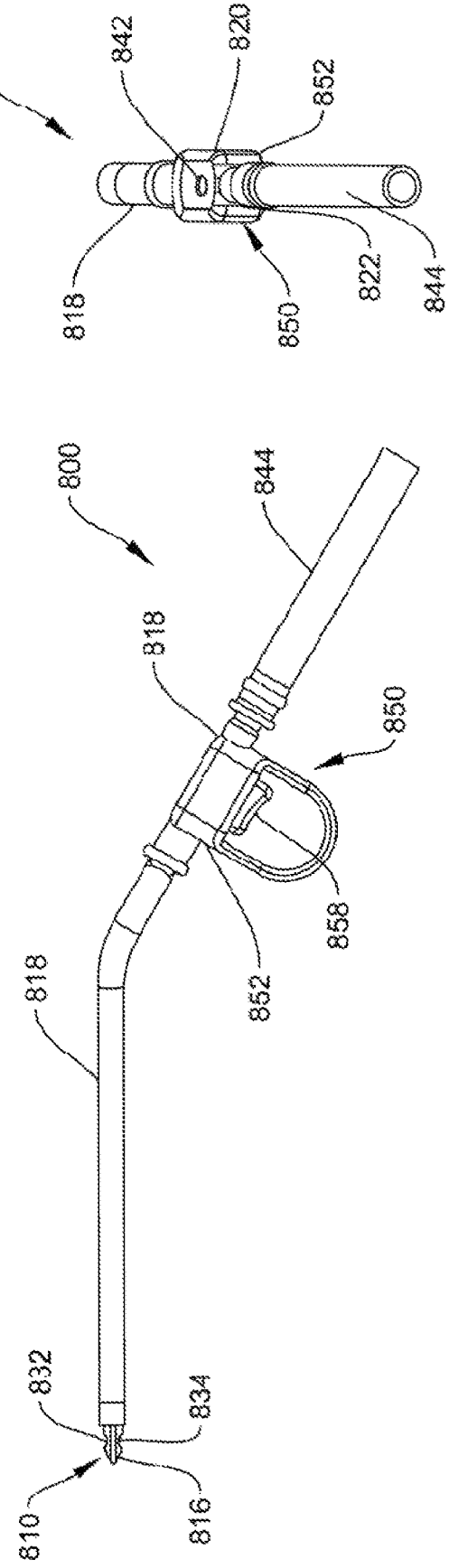

NASAL COAGULATION SUCTION DEVICE AND METHODS

CROSS-REFERENCE TO RELATED APPLICATION

This application is a continuation of U.S. application Ser. No. 15/722,928, filed Oct. 2, 2017, entitled NASAL COAGULATION SUCTION DEVICE AND METHODS which is a continuation-in-part of U.S. application Ser. No. 15/083,050, filed Mar. 28, 2016 and issued Oct. 3, 2017 as U.S. Pat. No. 9,775,673, entitled NASAL COAGULATION SUCTION DEVICE AND METHODS, and claims the benefit of the filing date of U.S. Provisional Application No. 62/138,579, filed Mar. 26, 2015, and entitled NASAL COAGULATION SUCTION DEVICE AND METHODS, the disclosures of which are incorporated herein, in their entireties, by this reference.

TECHNICAL FIELD

The present disclosure relates generally to medical devices and more particularly to nasal surgical devices and method for coagulation (and/or electrocautery) and suctioning during nasal surgery.

BACKGROUND

Sinus bleeding is one of the greatest obstacles faced by physicians practicing in the area of sinus/nasal surgery. Sinus bleeding is difficult to approach, often creates delays in surgeries, and can lead to costly complications.

Coagulation tools (also referred to as electrocauterization tools) utilize electrical energy to treat patient tissue such as bleeding sinus tissue. Coagulation procedures may be used to seal blood vessels during surgery to prevent blood flow. Ablation is utilized to vaporize or remove tissue using electrical energy. Coagulation probes may provide coagulation and ablation. Monopolar coagulation tools direct electric current from an active electrode of the tool through the patient's body and to a return electrode. The return electrode is usually defined by a grounding pad attached to the patient. Bipolar tools incorporate both an active and a return electrode into the tool.

A conductive irrigant such as saline is often used during surgical procedures utilizing bipolar tools. The saline solution provides a conduction path between the active and return electrodes of the tool. A high-frequency current delivered between the active and return electrodes effectively modifies tissue.

Some coagulation tools incorporate a suction feature to clear the surgical site of debris and other visual obstructions. The suction feature may be configured to permit a vacuum to be drawn through the tool from the distal end to a proximal point outside of the patient.

There has been an ongoing effort to reduce the size of surgical instruments whenever possible in order to reduce trauma to the patient. A number of challenges exist in creating a compact surgical instrument that includes both a suction tube as well as a coagulation feature. A further challenge related to coagulation tools having suction capability is clogging. When the treating portion or face of the coagulation electrode is in complete contact with tissue, suction through the opening into the suction tube can be temporarily stopped. This flow stoppage may result in the ablated tissue or other debris at the surgical location becoming lodges across the suction openings.

In view of these and other shortcomings related to existing coagulation suction devices, opportunities exist for improvements.

SUMMARY

One aspect of the present disclosure relates to a coagulation suction device (also referred to as an electrocauterization suction device) that includes a hollow suction tube, at least first and second bipolar wires, and an insulation cover. The hollow suction tube includes a closed distal tip, a proximal open end, and at least one suction opening positioned proximal of the closed distal tip. A position of the closed distal tip is adjustable relative to remaining portions of the hollow suction tube. The first and second bipolar wires extend along the hollow suction tube to the closed distal tip. The first and second bipolar wires each having an exposed distal end. The insulation cover encapsulates the first and second bipolar wires along a length of the first and second bipolar wires and terminates proximal of the exposed distal ends of the first and second bipolar wires.

The insulation cover may terminate proximal of the at least one suction opening. The at least one suction opening may include at least first and second suction openings. The at least first and second suction openings may be arranged opposite each other around a circumference of the hollow suction tube. The at least one suction opening may include an oblong shape. The first and second bipolar wires may be positioned on opposite sides of each other around a circumference of the hollow suction tube. The coagulation suction device may also include a suction control device positioned at a proximal end portion of the hollow suction tube. The suction control device may include a thumb actuated suction opening in flow communication with an interior of the hollow suction tube. The coagulation suction device may include a suction tubing attachment device positioned at the proximal open end of the hollow suction tube. The coagulation suction device may include a bipolar plug positioned at a proximal end of the first and second bipolar wires. The distal ends of the first and second bipolar wires may be exposed along a distal end surface of the closed distal tip of the hollow suction tube. The hollow suction tube may include a malleable material to provide adjustability of the closed distal tip relative to remaining portions of the hollow suction tube. The hollow suction tube and the insulation cover may comprise polymer materials. The insulation cover ma encapsulate the hollow suction tube proximally along at least a portion of a length of the hollow suction tube from a location proximal of the at least one suction opening.

Another aspect of the present disclosure relates to a coagulation suction device that includes a hollow suction tube, a plurality of bipolar wires, at least one suction opening, and an insulation cover. The hollow suction tube includes a closed distal tip located at a distal end portion thereof. The hollow suction tube includes a malleable portion to provide self-adjustment of an orientation of the closed distal tip internal a body cavity. An orientation of the closed distal tip may be adjustable from external the patient while the closed distal tip is located within a body cavity of the patient. The plurality of bipolar wires are each exposed along and terminate at the closed distal tip of the hollow suction tube. The at least one suction opening is formed in the hollow suction tube at the distal end portion at a location proximal of the closed distal tip. The insulation cover encapsulates the plurality of bipolar wires and hollow suction tube.

The coagulation suction device may include a suction control member positioned at a proximal end portion of the hollow suction tube and operable to control suction forces available at the at least one suction opening. The at least one suction opening may include a plurality of suction openings. The insulation cover may terminate proximal of the at least one suction opening. The closed distal tip of the hollow suction tube may define a hemispherical shape distal end surface of the hollow suction tube.

A further aspect of the present disclosure is directed to a method of manufacturing an coagulation suction device. The method includes providing a hollow suction tube, plurality of bipolar wires, and an insulation cover. The method also includes closing a distal tip of the hollow suction tube, forming at least one suction opening in a distal end portion of the hollow suction tube at a location proximal of the closed distal tip, arranging the plurality of bipolar wires along a least a portion of a length of the hollow suction tube with distal ends of the plurality of bipolar wires terminating at the closed distal tip, and encapsulating the plurality of bipolar wires with the insulation cover. The insulation cover is arranged so that the distal ends of the plurality of bipolar wires, the closed distal tip of the hollow suction tube, and the at least one suction opening are exposed.

The method may further include providing the hollow suction tube with an adjustable portion that provides adjustment of an orientation of the closed distal tip relative to other portions of the hollow suction tube. The method may include mounting a suction control device to a proximal end portion of the hollow suction tube, wherein the suction control device provides adjustment of a suction force available at the at least one suction opening. Forming at least one suction opening may include forming a plurality of suction openings in the distal end portion of the hollow suction tube.

Another embodiment is directed to a method of manufacturing a coagulation suction device. The method includes providing a catheter having at least one suction lumen, and a plurality of bipolar wires extending within the catheter along at least a portion of a length of the catheter, closing a distal tip of the catheter, forming at least one suction opening in a side surface of the catheter at a distal end portion of the catheter at a location proximal of the closed distal tip, and arranging distal ends of the plurality of bipolar wires between the closed distal tip and the at least one suction opening.

The method may also include providing a tip adjustable portion operable from a location outside of a patient to adjust an orientation of the closed distal tip. The method may include providing at least two pairs of bipolar wires. Forming at least one suction opening may include forming a plurality of suction openings in the distal end portion of the hollow suction tube. The method may include providing the catheter with a separate wire lumen to receive each of the plurality of bipolar wires. The method may include encapsulating portions of each of the plurality of bipolar wires in the catheter.

Another aspect of the present disclosure relates to a coagulation suction device having an insulation cover and first and second bipolar wires. The insulation cover has a distal end and a distal opening formed at the distal end, and a hollow cavity configured to receive a hollow suction tube. The first and second bipolar wires are encapsulated within the insulation cover and extend along the insulation cover to the distal end. The first and second bipolar wires extend distally beyond a distal-most surface of the insulation cover, and each have an exposed distal end. The exposed distal ends are bent toward each other and terminate adjacent to and spaced apart from each other.

The coagulation suction device may further comprise a suction tip that includes a closed distal end having a radius of curvature, the closed distal end extending distally beyond the distal end of the insulation cover, a proximal open end positioned in the hollow cavity of the insulation cover, and at least one suction opening positioned proximal of the closed distal end. The suction tip may be configured to be arranged in flow communication with the hollow suction tube when the hollow suction tube is received in the hollow cavity of the insulation cover. The insulation cover may terminate proximal of the at least one suction opening. The at least one suction opening may include at least first and second suction openings. The coagulation suction device may further include a trigger assembly mounted to a proximal end of the insulation cover, the trigger assembly operable to actuate the first and second bipolar wires. The trigger assembly may include a battery supply. The trigger assembly may include a wireless controller. The trigger assembly may include a housing sized to receive an on/off valve of the hollow suction tube. The coagulation suction device may further comprise wire leads electrically connected to the first and second bipolar electrodes, the wire leads being electrically connected to at least one electrode actuator.

Another aspect of the present disclosure relates to a coagulation suction device that includes an insulation cover, and a suction tip. The insulation cover has a hollow cavity and a distal end, and is configured to receive a suction tube. The suction tip is mounted in the hollow cavity and has a portion thereof extending distally beyond the distal end of the insulation cover. The suction tip includes a closed distal end having a radius of curvature, at least one suction opening positioned proximal of the closed distal end, and a plurality of bipolar wires encapsulated in the insulation cover. The bipolar wires have exposed distal ends extending along an outer surface of the suction tip, and the bipolar wires extend toward each other at the closed distal end and following the radius of curvature of the closed distal end.

The coagulation suction device may further comprise a housing mounted to a proximal end of the insulation cover, the housing configured to receive a suction control member of the suction tube. The at least one suction opening may include a plurality of suction openings. The suction tip may be configured to be in flow communication with the suction tube when the suction tube is received in the hollow cavity of the insulation cover. The coagulation suction device may further comprise a trigger assembly mounted to a proximal end of the insulation cover, the trigger assembly operable to actuate the first and second bipolar wires. The trigger assembly may include a battery supply. The trigger assembly may include a wireless controller. The trigger assembly may include a finger or thumb actuated trigger member.

A further aspect of the present disclosure relates to a method of operating a coagulation suction device. The method includes providing a coagulation suction device having a suction tip, a plurality of bipolar wires, and an insulation cover, the suction tip mounted to a distal end of the insulation cover, the plurality of bipolar wires extending through the insulation cover and having exposed distal ends positioned adjacent to the suction tip, and the exposed distal ends bending toward each other and following a contour of a closed distal surface of the suction tip. The method also includes mounting the coagulation suction device to a suction tube, the suction tube being in flow communication with the suction tip to provide suction flow at the suction tip, and actuating the plurality of bipolar electrodes to create a cauterizing zone at the suction tip.

The coagulation suction device may further includes a battery power source mounted to the insulation cover, and actuating the plurality of bipolar electrodes may include powering the plurality of bipolar electrodes with the battery power source. The method may further include concurrently applying the suction flow and the cauterizing environment.

Additional advantages and novel features of the invention will be set forth in the description which follows or may be learned by those skilled in the art through reading these materials or practicing the examples disclosed herein.

BRIEF DESCRIPTION OF THE DRAWINGS

The accompanying drawings illustrate various embodiments of the present invention and are a part of the specification. The illustrated embodiments are merely examples and do not limit the scope of the present disclosure.

FIG. 1 is a side view of an example surgical device in accordance with the present disclosure.

FIG. 2 is an end view of the surgical device shown in FIG. 1.

FIG. 3 is a cross-sectional view of the surgical device shown in FIG. 1 taken along cross-section indicators 3-3.

FIG. 4 is a cross-sectional view of a wire extension portion of the surgical device shown in FIG. 1 taken along cross-section indicators 4-4.

FIG. 8 is a side view of another example surgical device in accordance with the present disclosure.

FIG. 9 is an end view of the surgical device shown in FIG. 8.

FIG. 10 is a cross-sectional view of the surgical device shown in FIG. 8 taken along cross-section indicators 10-10.

FIG. 11 is a cross-sectional view of a suction control portion of the surgical device shown in FIG. 8 taken along cross-section indicators 11-11.

FIG. 14 is a cross-sectional view of another example surgical device having four internal lumens in accordance with the present disclosure.

FIG. 15 is a cross-sectional view of another example surgical device having five internal lumens in accordance with the present disclosure.

FIG. 16 is a side view of an end portion of another example surgical device in accordance with the present disclosure.

FIG. 17 is a top view of the end portion shown in FIG. 16.

FIG. 18 is an end view of the end portion shown in FIG. 16.

FIG. 20 is a perspective view of another example surgical device configured to mount to a suction tube having a bent construction.

FIG. 21 is an exploded perspective view of the surgical device show in FIG. 20.

FIG. 22 is a side view of the surgical device shown in FIG. 20.

FIG. 23 is a top view of the surgical device shown in FIG. 20.

FIG. 24 is an end view of the surgical device shown in FIG. 20.

FIG. 27 is a side view of the surgical device shown in FIG. 25.

FIG. 28 is a top view of the surgical device shown in FIG. 25.

FIG. 29 is a cross-sectional view of the surgical device shown in FIG. 25 taken along cross section indicators 29-29.

FIG. 30 is an rear end view of the surgical device shown in FIG. 25.

FIG. 33 is a side view of the surgical device shown in FIG. 31.

FIG. 34 is a top view of the surgical device shown in FIG. 31.

FIG. 35 is a cross sectional view of the surgical device shown in FIG. 34 taken along cross section indicators 35-35.

FIG. 36 is a rear end view of the surgical device shown in FIG. 31.

Throughout the drawings, identical reference numbers designate similar, but not necessarily identical, elements.

DETAILED DESCRIPTION

Figure 5:
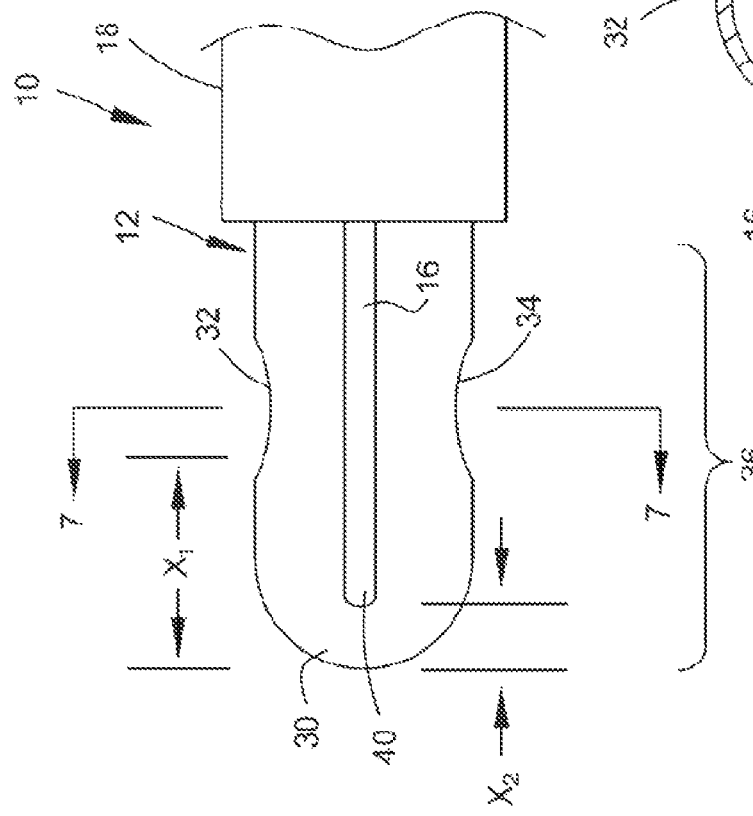
FIG. 5 is a close-up side view of an end portion of the surgical device shown in FIG. 1.
Figure 7:
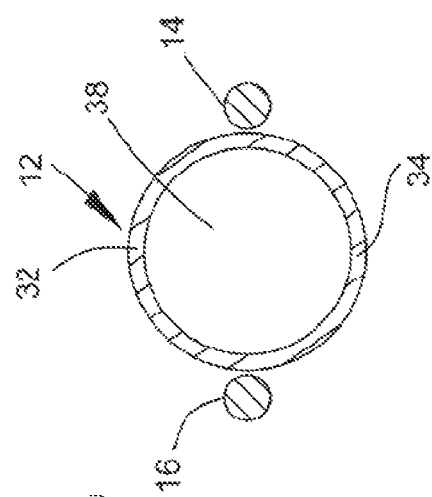
FIG. 7 is a cross-sectional view of the surgical device shown in FIG. 5 taken along cross-section indicators 7-7.

The present disclosure is directed primarily to surgical devices for use in nasal and sinus cavities. However, the principles disclosed herein may be generally applicable for use in treating other parts of the body. Generally, the surgical devices disclosed herein may be classified as coagulation devices and/or electrocauterization devices. The inclusion of suction capability with the surgical devices disclosed herein may classify the devices as coagulation suction devices. In at least some examples, the devices and/or methods disclosed herein may relate to nasal coagulation suction devices and related methods of treatment.

A number of challenges exist when working in the nasal and sinus cavities. For example, the sinuses are delicate and often difficult to work in because of their limited space and obscure location relative to an exterior of a patient. Operations in the sinuses pose the potential of damaging the optic nerve, frontal lobe, or other organs and/or vessels in the head. Bleeding in the sinuses and during sinus operations typically makes it difficult to observe the surgical site, thereby potentially decreasing accuracy and safety during surgery. Current methods of treating bleeding vessels in the sinuses are often too lengthy, complex, or ineffective. Cautery is often too aggressive and may cause excess damage to surrounding tissue. The nature of the sinuses is such that it may be difficult to navigate with currently known devices. Current methods and devices may introduce potential for additional errors, particularly when surgical technicians are carrying out the procedure. Additionally, current suction cautery devices and related methods locate cautery functions around the suction openings, which may cause clotting that blocks the suction opening.

The surgical devices of the present disclosure may include a bipolar cautery configuration which may provide improved cauterization as compared to a monopolar arrangement. The surgical devices may include a malleable and/or steerable tip that provides improved ease in navigating within the nasal and sinus cavities and may provide lower risk of damaging tissue while navigating to and from a surgical site. The malleable tip and/or features positioned thereon may be controllable without removing the device from the cavity. The malleable features may provide a self-orienting feature for the surgical device. In some embodiments, the surgical device may include a tip steering mechanism that provide a change in orientation and/or direction of the distal end portion of the surgical device from a location outside of the patient while the distal end portion is positioned in a body cavity of the patient. The surgical device may include suction which helps remove blood and debris at a surgical site. The suction openings may be positioned on one or more side surfaces of a suction tube of the surgical device. The suction openings may be spaced proximal of a distal tip of the surgical device, and may be positioned proximal of the bipolar cautery wires (i.e., tips of the bipolar cautery wires). The surgical device may have a relatively small profile in the range of about, for example, 3 F to about 10 F, and more preferably in the range of about 6 F to about 8 F. The distal tip of the surgical device may include a nonstick coating that limits collection of tissue, debris, and the like. In at least one example, the nonstick coating includes Teflon®.

The present description provides examples, and is not limiting of the scope, applicability, or configuration set forth in the claims. Thus, it will be understood that changes may be made in the function and arrangement of elements discussed without departing from the spirit and scope of the disclosure, and various embodiments may omit, substitute, or add other procedures or components as appropriate. For instance, the methods described may be performed in an order different from that described, and various steps may be added, omitted, or combined. Also, features described with respect to certain embodiments may be combined in other embodiments.

Referring first to FIGS. 1-7, and particularly FIG. 1, a surgical device 10 is shown and described. The surgical device 10 may be a coagulation suction device. The surgical device 10 may be particularly useful within the nasal and sinus cavities of a patient, although it may be used in other applications, such as for treatment of a patient at other locations within the body. Certain features of the surgical device 10 may be modified for use in treating other aspects of a patient. For example, an insertion length of the surgical device 10 may be increased when the surgical device is to be used to treat the esophagus or stomach of a patient, or may be reduced in length when the surgical device is used to treat cavities closer to an exterior surface of the patient.

Surgical device 10 may include a suction tube 12, a pair of bipolar wires 14, 16, an insulation cover 18, a suction control member 20, a suction tubing attachment 22, a wire extension 24, and a wire plug 26, as shown in FIG. 1. The surgical device 10 may include an insertion portion having a length $L_1$. The surgical device 10 may have a profile at a location along its length $L_1$ having a width W and a thickness T, as shown in FIG. 2. The width W and thickness T may be substantially the same in some embodiments, whereas in other embodiments, such as the one shown in FIG. 2, the width W is greater than the thickness T. In at least some embodiments, the maximum dimension of a cross-section of the surgical device 10 (e.g., the width W in the embodiment shown in FIG. 2) is in the range of about 3 F to about 10 F, and more particularly in the range of about 6 F to about 7 F. Other maximum cross-sectional dimensions may be possible including dimensions greater than 10 F (e.g., in the range of about 10 F to about 20 F). Further, smaller sizes may be possible as improvements are made in materials, manufacturing, and the like to provide sizes less than 3 F (e.g., in the range of about 1 F to about 3 F).

The suction tube 12 may include a tip 30, a pair of suction ports 32, 34 positioned opposite each other around a circumference of the suction tube 12, and an exposed portion 36 that is arranged distal of a distal most point of the insulation cover 18. Further, suction tube 12 may include a suction lumen 38 (see FIG. 3). The suction ports 32, 34 may be in flow communication with suction lumen 38 as well as the suction control member 20 and the suction tubing attachment 22. An operator may control the amount of suction force available at the suction ports 32, 34 by operating the suction control member 20. Suction control member 20 may include an opening 42 that the operator covers or partially covers with a thumb, finger or other object to control the suction force applied at suction ports 32, 34. Opening 42 may be in flow communication with the suction lumen 38 of suction tube 12.

The suction ports 32, 34 may be spaced proximal of the distal tip 30 a distance $X_1$ (see FIG. 5). The distance $X_1$ may be in the range of about 1 mm to about 20 mm, and more particularly in the range of about 2 mm to about 5 mm. The suction ports 32, 34 may have a diameter (e.g., maximum dimension) in the range of about 0.1 mm to about 10 mm, and more particularly in the range of about 1 mm to about 7 mm.

Figure 6:
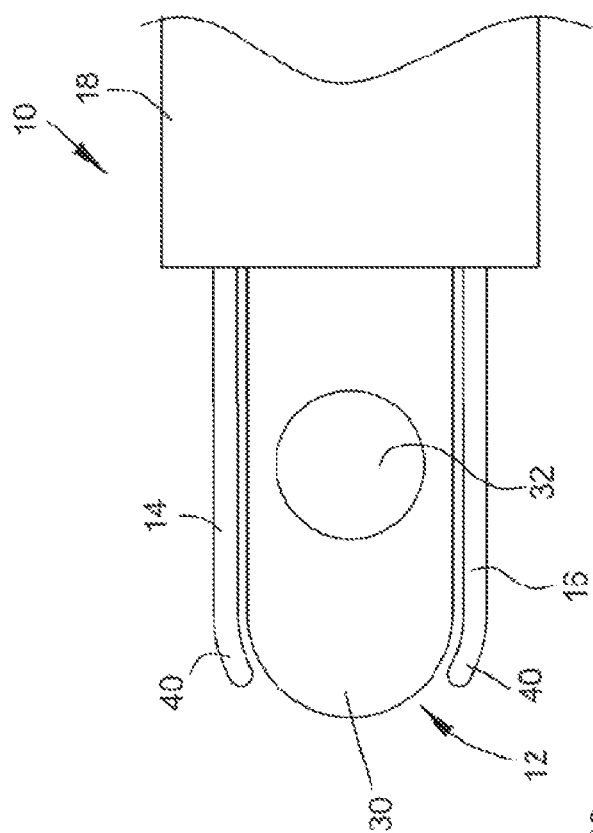
FIG. 6 is a close-up top view of the end portion of the surgical device shown in FIG. 1.

The suction ports 32, 34 may also be positioned proximal of distal ends 40 of bipolar wires 14, 16 (see FIG. 6). The arrangement of suction ports 32, 34 at a location proximal of the tip 30 and distal ends 40 of the bipolar wires 14, 16 may limit potential problems of clogging the suction ports 32, 34 with coagulated blood, cauterized tissue, or other debris or objects located in the area of a surgical site. The suction ports 32, 34 are shown having a generally circular shape as shown in at least FIG. 6. Other shapes and sizes are possible for the suction ports 32, 34 including, for example, oval shaped profiles.

The suction ports 32, 34 are located on opposite side surfaces of suction tube 12 (see FIG. 5). The suction port 32 may be positioned along a top side of the surgical device 10 and be referred to as a superior suction port 32. The suction port 34 may be positioned along a bottom side of the surgical device 10 and be referred to as an inferior suction port 34. The suction ports 32, 34 are located at a common longitudinal point along the length of suction tube 12. Other arrangements are possible in which the suction ports 32, 34 are offset longitudinally relative to each other, positioned at other circumferential locations relative to each other besides at direct opposite positions, and may be positioned at various circumferential and longitudinal positions relative to the distal ends 40 of bipolar wires 14, 16 and tip 30. In some arrangements, distal ends 40 of the bipolar wires 14, 16 are positioned offset longitudinally relative to each other, and the suction ports 32, 34 are offset longitudinally relative to each other and/or relative to the distal ends 40 of bipolar wires 14, 16.

Figure 13:
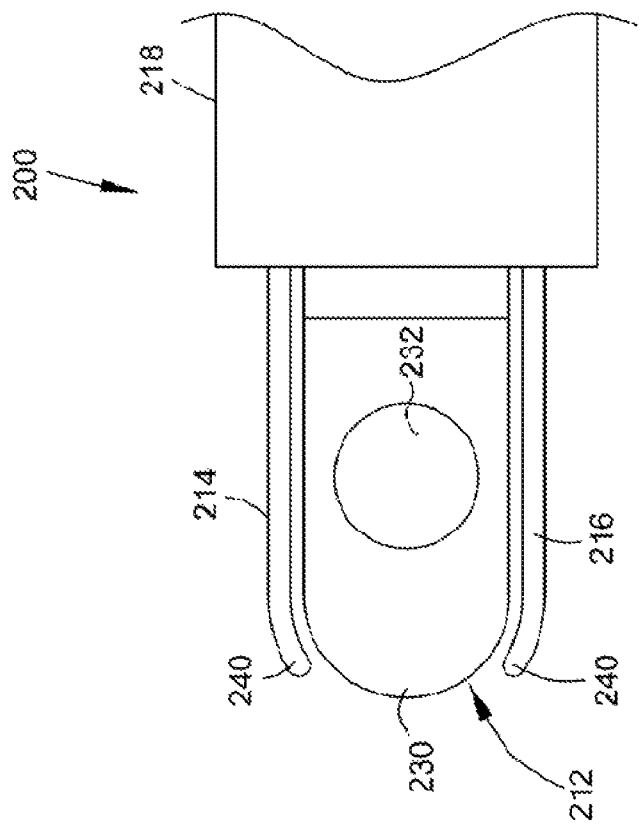
FIG. 13 is a close-up top view of the end portion of the surgical device shown in FIG. 8.
Figure 12:
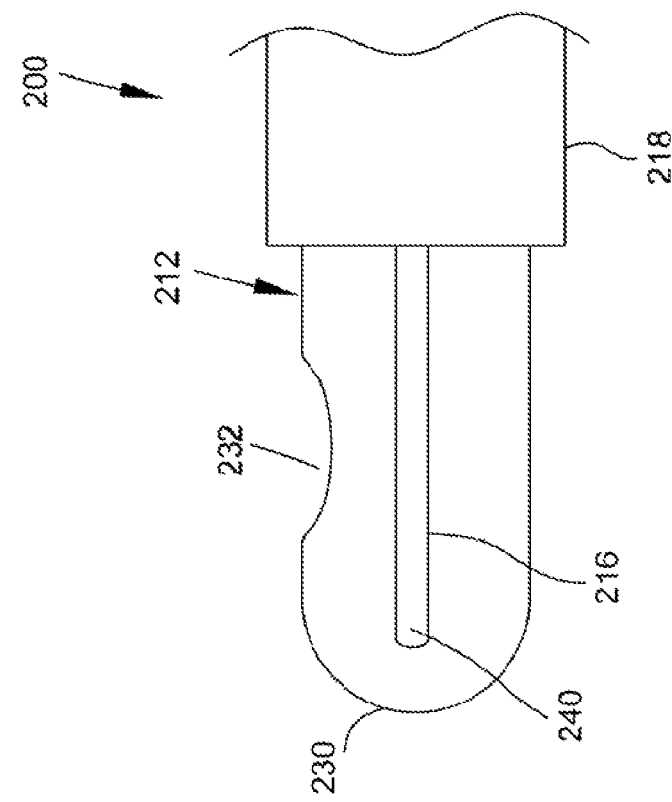
FIG. 12 is a close-up side view of an end portion of the surgical device shown in FIG. 8.

Other embodiments are possible in which more than two suction ports 32, 34 are included on a single suction tube 12. For example, three or more suction ports may be positioned at a common longitudinal position along the length of suction tube 12 and offset equally around a circumference of suction tube 12. In still further examples, a single suction port is included on suction tube 12. For example, FIGS. 12 and 13 show a surgical device 200 that includes a single suction port 232 formed in suction tube 212. The single suction port 232 is positioned proximal of distal ends 240 of bipolar wires 214, 216, and proximal of the distal tip 230 of suction tube 212. Suction port 232 is positioned distal of a distal most end of insulation cover 218. Further, suction port 232 is shown including a circular profile (see FIG. 13), but may include other shapes, sizes and orientations in other embodiments.

Referring again to FIGS. 1-7, the suction tube 12 includes an exposed portion 36 that extends distally beyond a distal most point of insulation cover 18. Exposed portion 36 has a length $L_E$ as shown in FIG. 1. The length $L_E$ may vary depending on a variety of factors including, for example, the size and shape of suction ports 32, 34, the size and shape of distal tip 30, the size, shape and orientation of bipolar wires 14, 16 and their distal ends 40, and the like. In one example, the length $L_E$ is in the range of about 1 mm to about 20 mm, and more particularly in the range of about 2 to about 10 mm.

The distal ends 40 of bipolar wires 14, 16 are typically spaced proximal of a distal most end of tip 30. FIG. 5 shows distal ends 40 spaced a distance $X_2$ from the distal most tip 30. The distance $X_2$ may be in the range of about 0.5 mm to about 2 mm, and more particularly about 0.1 mm to about 1 mm. The distal ends 40 may include and/or be formed as a bulbous portion and/or have a spherical shaped portion. Distal ends 40 may be specifically sized, arranged and/or configured to provide improved cauterization of tissue. The distal ends 40 may be positioned at tip 30 or may extend distally beyond tip 30. The bipolar wires 14, 16 may be adjustable axially to position distal ends 40 at various positions relative to tip 30 during delivery and/or operation of surgical device 10.

In some embodiments, the suction tube 12 comprises a metallic material or other electrically conductive material (e.g., stainless steel). In other embodiments, the suction tube 12 comprises a polymer material such as Pebax®, polyurethane or polypropylene. The suction tube 12 may comprise the same material as the insulation cover 18. In some embodiments, the suction tube 12 is a continuous, integrally formed structure with the insulation cover 18 (e.g., formed by co-extrusion, co-molding, heat forming, or the like). The suction tube 12, or at least the tip 30 positioned adjacent to distal ends 40, may provide a conducting surface between the distal ends 40 of the bipolar wires 14, 16. In at least some examples, the bipolar wires 14, 16 comprise a conductive metallic material such as, for example, copper. Other suitable materials for bipolar wires 14, 16 include Aluminum.

Operation of bipolar wires 14, 16 to provide coagulation and/or cauterization may be controlled from a remote location. The bipolar wires 14, 16 may extend within insulation cover 18 along the insertion length $L_I$ along the length of suction tube 12. At some point proximal of the insertion length $L_I$, the bipolar wires 14, 16 may detach from suction tube 12 as wire extension 24. Wire extension 24 may connect with a control member via wire plug 26. The control member may include, for example, a foot-actuated pedal or other control device. The actuator may control the amount of power supplied to the distal ends 40 for purposes of cauterizing or otherwise treating tissue (e.g., a vessel) at a surgical site.

The surgical device 10 is shown including a single pair of bipolar wires 14, 16. Other embodiments may include more than two bipolar wires 14, 16, such as two or more pairs of bipolar wires 14, 16. The pairs of bipolar wires 14, 16 may terminate at different distal locations along the length of suction tube 12. For example, one pair of bipolar wires 14, 16 may terminate at distal tip 30, while other pairs of bipolar wires 14, 16 may terminate at locations spaced between distal tip 30 and suction ports 32, 34, or at locations proximal of suction ports 32, 34.

The insulation cover 18 may encapsulate the bipolar wires 14, 16 except in the area of distal ends 40 where the bipolar wires 14, 16 are exposed for the purpose of cauterizing or otherwise treating tissue. Insulation cover 18 may comprise a polymer material such as, for example, polypropylene, polyurethane, FEP (fluorinated ethylene propylene), or Pebax® thermoplastic elastomer material. In at least some examples, bipolar wires 14, 16 and suction tube 12 are co-molded together within insulation cover 18. Insulation cover 18 may be referred to as a catheter or a catheter member. Typically, insulation cover 18 comprises an electrically nonconductive material. Insulation cover 18 provides an insulation layer between the suction tube 12 and the bipolar wires 14, 16 along at least the insertion portion having length $L_I$. The bipolar wires 14, 16 may be referred to as lateral and medial bipolar wires 14, 16, respectively, or may be referred to as opposed bipolar wires 14, 16 (e.g., arranged on opposite sides of tip 30). FIG. 3 shows a cross-sectional view of the insertion portion of surgical device 10 and at least a portion of the insulation cover 18 interposed between the suction tube 12 outer surface and the bipolar wires 14, 16. FIG. 4 shows the insulation cover 18 providing an insulating layer between bipolar wires 14, 16 along at least the wire extension 24.

The surgical device 10 may include a malleable distal portion 28 (see FIG. 1). The distal portion 28 may be malleable in the sense that it can be shaped, altered in orientation, and/or comprise flexibility properties. The malleable nature of distal portion 28 may provide for improved navigation around corners and through otherwise tortuous paths in the body, such as through nasal and sinus cavities. Distal portion 28 may include materials that provide at least some malleability for the surgical device 10. Distal portion 28 may include shapes and sizes that also provide malleability properties for surgical device 10. For example, tip 30 may include a bulbous construction as shown in FIGS. 2, 5 and 6. The bulbous construction of tip 30 may provide less friction and/or obstructions at the distal end of surgical device 10 that provides improved navigation through bodily cavities within which surgical device 10 is used. Tip 30 may be defined as having a hemispherical or spherical shaped construction. Malleable distal portion 28 may have a length $L_M$. Surgical device 10 may include structural features such as, for example, reduced material thicknesses, different material compositions, and the like that provide improved malleability of distal portion 28 as compared to other portions of surgical device 10 that are located proximal of distal portion 28.

In some embodiments, malleable distal portion 28 may include a coating along at least portions thereof. The coating may comprise a nonstick or low friction property. In one example, the coating comprises Teflon® or other low surface friction material. Other example coating materials include Pebax, Peek (polyetheretherketone), PEG (polyethylene glycol), and other medical coatings available from, for example, Hydromer® of Branchburg, N.J. Another suitable coating material includes a stimulus-responsive polymer such as N-isopropyl acrylamide (NIPAAm) or other thermally or electro-responsive polymer to provide a low friction surface.

In at least some examples, the tip 30 of suction tube 12 comprises a different material than the remaining portions of suction tube 12. For example, the hemispherical shaped tip 30 may comprise a material having a lower density, softer feel, lower friction, or other property. For example, tip 30 may comprise a polymer material (or a first polymer material) while the remaining portions of suction tube 12 comprise a metal material or second polymer material, wherein the material of the remaining portions of the suction tube 12 provides the desired properties for suction and for operation of the bipolar electrodes to create coagulation and/or hemostasis at a surgical site.

Generally, the materials, shape, size and other characteristics of tip 30 and/or distal portion 28 generally, provide reduced tissue adhesion during coagulation. In some embodiments, the tip 30 may have a relatively rigid construction to assist in navigating passages and cavities of the body.

The length $L_M$ of the distal portion 28 is typically in the range of about 0.5 cm to about 5 cm, and more preferably in the range of about 1 cm to about 4 cm. The distal portion 28 may have malleable properties to provide improved self-adjustment of an orientation and/or shape of the distal portion 28 while navigating passages and cavities of the body. The distal portion 28 may be steerable or include steerable properties. An orientation of distal portion 28 may be adjustable from a location outside of the patient while the distal portion 28 is positioned within a body cavity. In some embodiments, the distal portion 28 may be adjusted into a certain shape or orientation while positioned outside of the patient and maintain that shape or orientation when inserted into a body cavity. This may be referred to as a shape memory property. In yet other embodiments, the distal portion 28 may include a shape memory material that takes on a different shape or orientation when inserted into a body cavity. The shape memory material may take on a different shape and/or orientation when exposed to a certain temperate (e.g., a temperature activated material that changes shape when heated to body temperature), or when exposed to an electrical stimulus (e.g., an electrical activated material that changes shape when stimulated with an electrical charge).

Referring now to FIGS. 8-11, another example surgical device 100 is shown and described. Surgical device 100 may include many of the same or similar features as described above with reference to surgical device 10. For example, surgical device 100 includes a suction tube 112, a pair of bipolar wires 114, 116, an insulation cover 118, a suction control member 120, a suction tubing attachment 122, a wire extension 124, and a wire plug 126. The surgical device 100 may include a malleable distal portion 128.

The suction tube 112 may include a tip 130, first and second suction ports 132, 134, and a suction lumen 138 (see FIG. 10). In some embodiments, the suction tube 112 is formed integral as a single piece with the insulation cover 118. The bipolar wires 114, 116 may each include a distal end 140.

The insulation cover 118 may be configured as a catheter type structure with a plurality of lumens 150, 152, 154 (see FIGS. 10 and 11). The lumen 150 is sized for insertion of suction tube 112. In some embodiments, lumen 150 takes the place of suction tube 112, wherein a suction force is applied directly within lumen 150. Insulation cover 118 may be referred to as a multi-lumen catheter. In some embodiments, insulation cover 118 may have a modified shape at its distal end in which lumens 152, 154 are eliminated (e.g., to exposed distal end portions of bipolar wires 114, 116), and the suction ports 132, 134 are formed in side surfaces of insulation cover 118 to provide access into lumen 150 where a suction force is applied.

Lumens 152, 154 are sized to receive the bipolar wires 114, 116. In at least some examples, the suction tube 112 and bipolar wires 114, 116 may be able to advance and retract longitudinally relative to the lumens 150, 152, 154 of insulation cover 118. Insulation cover 118 may be referred to as a tri-lumen device and/or catheter. The surgical device 100 may be assembled by inserting the suction tube 112 and bipolar wires 114, 116 into insulation cover 118 (e.g., as compared to co-molding, bonding, or other forming methods that may be possible).

The lumens 150, 152, 154 are shown in at least FIGS. 10 and 11 arranged side-by-side across a width of the insulation cover 118. Other arrangements are possible for positioning of the lumens 150, 152, 154 relative to each other. Further, the size and shape of the lumens 150, 152, 154 may be modified as desired to accommodate different sizes, cross-sectional shapes, materials, and the like for any of the suction tube 112, bipolar wires 114, 116 and other devices inserted therein.

Any of the lumens 150, 152, 154 may be provided with a greater diameter or other internal dimension as compared to the diameter or other outer dimension of the device inserted therein. A space or cavity may be interposed between the inner surface of the lumens and the respective component inserted therein. This cavity or space may be used to deliver other objects or materials to a surgical site. In at least one example, a cavity provided between an outer surface of suction tube 112 and an inner surface of lumen 150 may provide a delivery passage for saline or other fluid to be delivered to a surgical site. In another example, another device may be inserted over an exterior of any one of suction tube 112 and bipolar wires 114, 166 and within a respective lumen 150, 152, 154. In a still further example, a device may be inserted within the internal suction lumen 138 of suction tube 112 for delivery to a surgical site. Such a device may travel through suction lumen 138 and out of suction ports 132, 134. In still further examples, a fluid may be delivered to the surgical site via the suction lumen 138 of suction tube 112, for example, prior to applying a suction force within suction lumen 138. In other embodiments, a fluid may be delivered through any of the lumens 150, 152, 154 of insulation cover 118.

FIG. 8 shows another example suction control member 120 that is positioned over both the insulation cover 118 as well as the suction tube 112. FIG. 11 shows a cross-sectional view of surgical device 100 in which the opening 142 is shown in flow communication with the suction lumen 138 to provide manual control of an amount of suction force applied at suction ports 132, 134. Other control mechanisms and/or features may be possible in place of or in combination with manually controlled opening 142. In some embodiments, suction control member 120 may provide a structure for separating the bipolar wires 114, 116 and associated insulation cover 118 from the suction tube 112. FIG. 8 shows the wire extension 124 separating from the insulation cover 118 at a location adjacent to suction tubing attachment 122. Many other embodiments and configurations are possible for separating the wire extension 124 from suction tube 112 and insulation cover 118. In some examples, the bipolar wires 114, 116 are encapsulated within wire extension 124, whereas in other embodiments the wire extension 124 includes separate lumens within which the bipolar wires 114, 116 are positioned. The wire extension 124 may be considered a multi-lumen catheter that carries the bipolar wires 114, 116.

FIGS. 14 and 15 illustrate further example surgical devices 300, 400 that include additional lumens. FIG. 14 shows a surgical device 300 having four lumens 350, 352, 354, 356 formed in an insulation cover 318. The lumen 350 carries a suction tube 312. The lumens 352, 354 carry bipolar wires 314, 316. The lumen 356 may be used for various purposes including, for example, delivery of a fluid to a surgical site at a distal end portion of the surgical device 300. Lumen 356 may be used to deliver another device and/or component such as, for example, a light fixture, a camera, a gripping or grasping member, a guidewire, a gauze member, medications, pressurized air, a needle, a cutting device, or the like. Various instruments or other materials may be inserted into and removed from lumen 356 prior to, during, and/or after treatment of tissue at a surgical site using surgical device 300.

FIG. 15 shows a surgical device 400 having an insulation cover 418 (also referred to as a catheter 418) with five lumens 450, 452, 454, 456, 458. Lumen 450 may receive suction tube 412. Lumens 452, 454 may receive bipolar wires 414, 416. Lumen 456 and 458 may receive or deliver various materials, components, instruments, and the like to or from a surgical site. FIG. 15 shows the lumen 456 empty, although lumen 456 may be filled with a fluid such as a medication, saline solution, pressurized gas, or the like. Lumen 458 is shown including a device 460 and a wire 462. In one example, the device 460 comprises a light or camera. The wire 462 may provide power to the light or camera. In another example, the device 460 and/or wire 462 may be part of a tip control mechanism used to control an orientation of the distal tip of the suction tube 412 and or distal end portion of the surgical device 400 generally. The tip control mechanism may be operable from outside of the patient while the surgical device 400 is positioned within a body cavity of a patient.

Either one of the lumens 456, 458 may be used to deliver instruments, fluids, drugs, or other components needed to carry out a procedure. In some examples, the lumens 456, 458 may be receptive of additional bipolar wires whose distal tips are exposed at a distal end portion of the surgical device 400 (e.g., at distal tip of suction tube 412 or at a location spaced between the distal tip of suction tube 412 and the suction ports of the suction tube 412). For example, wire 462 may be a bipolar wire that is used for coagulation and/or electrocauterization. In other embodiments, a plurality of bipolar wires may extend through any one of or a multiple ones of the lumens 450, 452, 454, 456, 458. The bipolar wires may each include a separate insulation cover to provide electrical insulation from other bipolar wires positioned within a common lumen of the catheter 418. Each bipolar wire or pair of bipolar wire may be separately controlled to provide an operator with many options for treating tissue at an operation site (e.g., increasing or decreasing a cauterizing field).

FIG. 14 shows the surgical device 300 having a generally elliptical shaped cross-section while surgical device 400 shown in FIG. 15 has a circular shaped cross-section. The cross-sectional shape of any of the surgical devices disclosed herein may be modified to provide a minimum, lowest profile shape and size possible while still providing the desired number, shape and size of lumens and/or an amount of insulating material needed for purposes of carrying out a coagulation suction procedure using the surgical device. One potential advantage of the surgical devices disclosed herein is the reduced profile and the use of a single, compact device for insertion through the nasal and sinus cavities to the surgical site. Even when an insulating cover and/or catheter having a plurality of lumens is used, all of the lumens and the related devices carried in the lumens are consolidated within a single instrument that is inserted into the patient. This use of a single instrument may reduce the complexity of the procedure and provide other advantages such as, for example, reduced damage to tissue when entering and exiting the nasal and sinus cavities, being able to insert and/or operate the surgical device with a single hand or by a single person, and easier navigation to a surgical site.

FIGS. 16-18 show an end portion of another example surgical device 500. The surgical device includes two pairs of bipolar wires 514a, 516a and 514b, 516b, a multi-lumen catheter 518 (also referred to as an insulation cover 518), and steering mechanisms 570, 572.

The bipolar wires 514a, 516a and 514b, 516b may be positioned spaced apart around a circumference of catheter 518 at distal portion 528. Each pair of bipolar wires 514a, 516a and 514b, 516b may be positioned opposite each other along an exterior of the catheter 518. The bipolar wires 514a, 516a and 514b, 516b may terminate at different distal locations relative to a tip 530 of catheter 518. For example, bipolar wires 514a, 516a may terminate closer to suction ports 532, 534 of catheter 518, while bipolar wires 514b, 516b may terminate closer to tip 530. In other examples, the bipolar wires 514a, 516a and 514b, 516b all terminate at approximately the same longitudinal position along the length of the surgical device 500 (e.g. position relative to tip 530). The bipolar wires 514a, 516a and 514b, 516b may all terminate at locations between tip 530 and suction ports 532, 534. In other embodiments, one or more of the bipolar wires 514a, 516a and 514b, 516b may terminate at a location spaced distal of tip 530 or at a location spaced proximal of one or more of suction ports 532, 534.

The bipolar wires 514a, 516a and 514b, 516b may be individually controllable to provide cauterization and/or coagulation at a treatment site. In one example, the pair of bipolar wires 514b, 516b may be operable for a first period of time, and when the operator additionally operates the pair of bipolar wires 514a, 516a when he would like to increase a magnitude of cauterization. The operator may turn off either pair of bipolar wires 514a, 516a and 514b, 516b when he would like to reduce the magnitude of cauterization. When the bipolar wires 514a, 516a and 514b, 516b terminate at different locations relative to tip 530, the operator may operate different one of the bipolar wires 514a, 516a and 514b, 516b to cauterize at specification locations without having to adjust an axial position of surgical device 500. When the bipolar wires 514a, 516a and 514b, 516b all terminate at a common axial position, the operator may operate certain ones of the bipolar wires 514a, 516a and 514b, 516b to provide cauterization at specification circumferential locations at the treatment site. In some embodiments, additional pairs of bipolar wires may be used at any desired location, orientation, and the like to optimize or customize the cauterization/coagulation options available to the operator.

The catheter 518 may include steering lumens 562, 564 that receive steering mechanisms 570, 572, respectively. The catheter 518 may also include a suction lumen (not shown) that is in flow communication with the suction ports 532, 534. The suction lumen may be an example of the suction lumen 38 shown in FIG. 1 or the tube lumen 150 shown in FIG. 10. The catheter 518 may be provided as a single piece that is either bonded or connected together as a single piece (e.g., co-molded, heat bonded, or the like), or extruded as a single piece.

The steering mechanisms 570, 572 may be connected to catheter 518 at a distal connection point 574. The steering mechanisms 570, 572 may extend to a proximal end of the surgical device 500 where the steering mechanisms 570, 572 are operable at a location outside of the patient. In at least one example, applying an axial force at a proximal end portion of steering mechanisms 570, 572 may cause the tip 530 to change shape (e.g., change from a straight shape to a bent or curved shape) or change direction or orientation (e.g., point to one side or another). Many other types of steering mechanisms, systems, devices and the like may be used with any of the surgical devices disclosed herein. For example, a handheld mechanical or electronically operated trigger member may be used to actuate the steering mechanisms 570, 572. The steering mechanism are typically operable from outside of a body cavity to remotely reposition a distal end portion of the surgical device, or change a shape thereof, to help navigate the surgical device through body passages and cavities.

The distal end portion 528, or portions thereof, of surgical device 500 may include malleable materials or have malleable properties. The malleable properties of distal end portion 528 may provide at least some automatic or self-initiated change of orientation or shape of the surgical device while navigating through the body. The surgical device 500 may include a distal end portion 528 that is both malleable and steerable.

Referring now to FIGS. 19-36, additional surgical device embodiments are described. The embodiments of FIGS. 19-36 may be particularly suited for removably mounting to an existing suction tube device, such as, for example, a Karl Storz Ferguson suction tube (also referred to as a "Karl Storz suction tube"). The embodiments of FIGS. 19-36 may be configured as disposable or limited use devices. The embodiments of FIGS. 19-36 may have the same or similar functionality and operation as the embodiments of FIGS. 1-18 described above. The features and details described above with reference to FIGS. 1-18 may be applicable in whole or in part to the embodiments of FIGS. 19-36.

In order to provide both easy integration into the operating room and to reduce the cost of material burden, the embodiments of FIGS. 19-36 may be modified and/or configured to be integrated into a flexible device that acts as a sleeve or external fixation device capable of use with a pre-existing device. In one example, the surgical device having a sleeve-shaped portion may be slid onto a suction device, such as the Karl Storz suction tube described above. A surgical device having such a sleeve or external fixation feature may be also be flexible and act as an external covering over an otherwise relatively rigid device such as a suction wand. This pre-existing rigid device may already have an integrated suction capability, such as a suction opening located at a tip of the pre-existing rigid device. The pre-existing rigid device may also have a mechanism to control the suction at a base of the device. The surgical devices disclosed herein may have a closed distal tip with a proximal open end to act as a suction opening that is in flow communication with a suction tube or other suction feature of the pre-existing device. The surgical devices disclosed herein may also include first and second bipolar wires (or three or more bipolar wires) extending along a hollow flexible tube or sheath to a closed distal tip of the surgical device. The bipolar wires may each have an exposed distal end. These exposed distal ends may converge towards each other at a distal tip of the surgical device. The bipolar wires may generate a cauterization area or zone for use in treating a patient (e.g., cauterizing a vessel). As discussed herein, providing an insulation cover that encapsulates the bipolar wires along a majority of a length of the bipolar wires help maintain separation of the bipolar wires until a distal tip region of the device. The insulating cover or sleeve may terminate at a location proximal of the exposed distal ends of the bipolar wires. The sleeve may be able to slide on and off of the distal end of the existing suction devices as described herein. Further, the sleeve may be sized with an internal cavity that fits relatively closely to an external dimension of the pre-existing suction device, in particular with an interface that provides a reduced friction interface that avoids damaging the sleeve, but enough resistance to maintain the sleeve in place positioned on the pre-existing suction device.

The surgical devices disclosed with reference to FIGS. 19-36 may include embodiments in which the surgical device, including the sleeve and bipolar wires, releasably connects to a pre-existing device using, for example, a clamp, fastener, or the like. Alternatively, the surgical device may be permanently connected to a pre-existing device (e.g., a pre-existing suction device). In another embodiment, the energy source used to operate the bipolar wires to generate, for example, a cautery function for the surgical device, may be provided from a battery power source. The battery power source may be located, for example, at a base of the surgical device rather than requiring wires that would otherwise extend from the surgical device, for example, an electrode cautery box, as is typically done with electro-cautery devices. Using a battery power source may also allow the surgical device to be free of additional wires that would otherwise be needed to carry out a procedure.

In another embodiment, the activation trigger or button for operating the electro-cautery features (e.g., powering the bipolar wires) may be located at the base or proximal end of the surgical device rather than using a traditional foot pedal. Control features for the surgical device may also be mounted to the device itself, for example, at a base or proximal end of the insulating cover or sleeve. The control features may include, for example, a processor, memory, transceiver and trigger. The control features may include a wireless controller that generates and receives wireless signals. The wireless signals may be used to communicate with a remote device, such as, for example, a computer network, a foot pedal, a power source, or other control mechanism.

Figure 19:
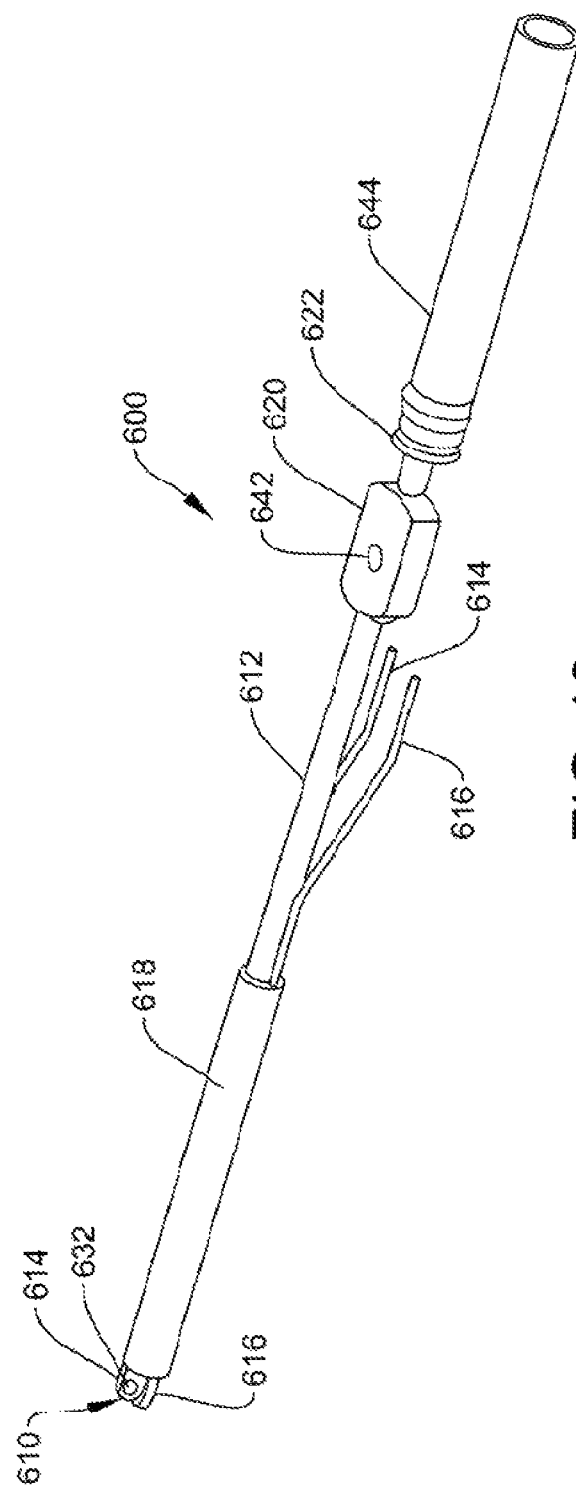
FIG. 19 is a perspective view of another example surgical device configured to mount to a suction tube having a straight construction.
Figure 25:
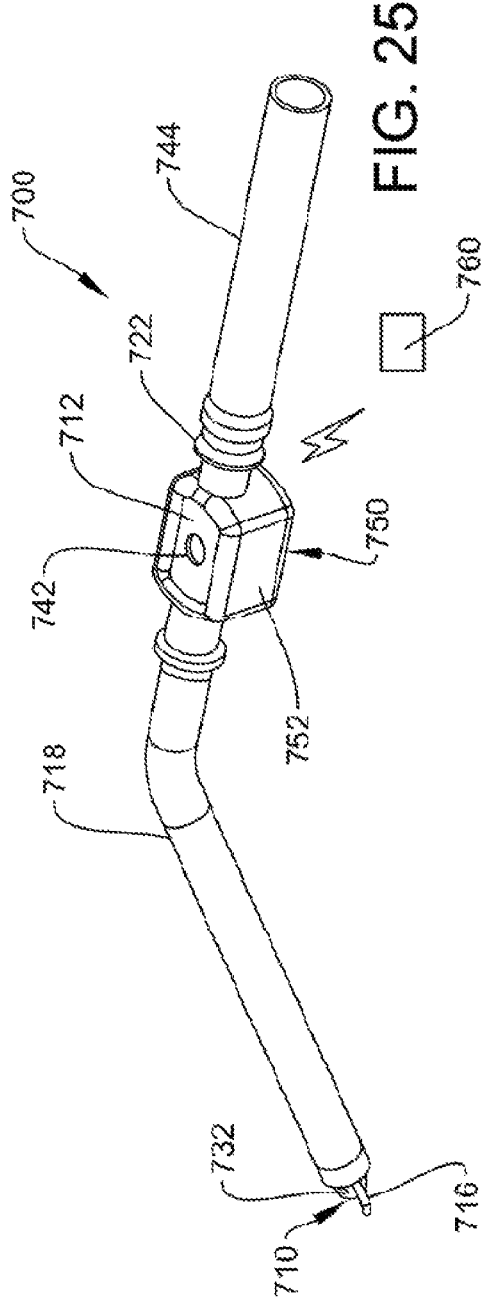
FIG. 25 is a perspective view of another example surgical device configured to mount to a suction tube and having a battery power source.
Figure 26:
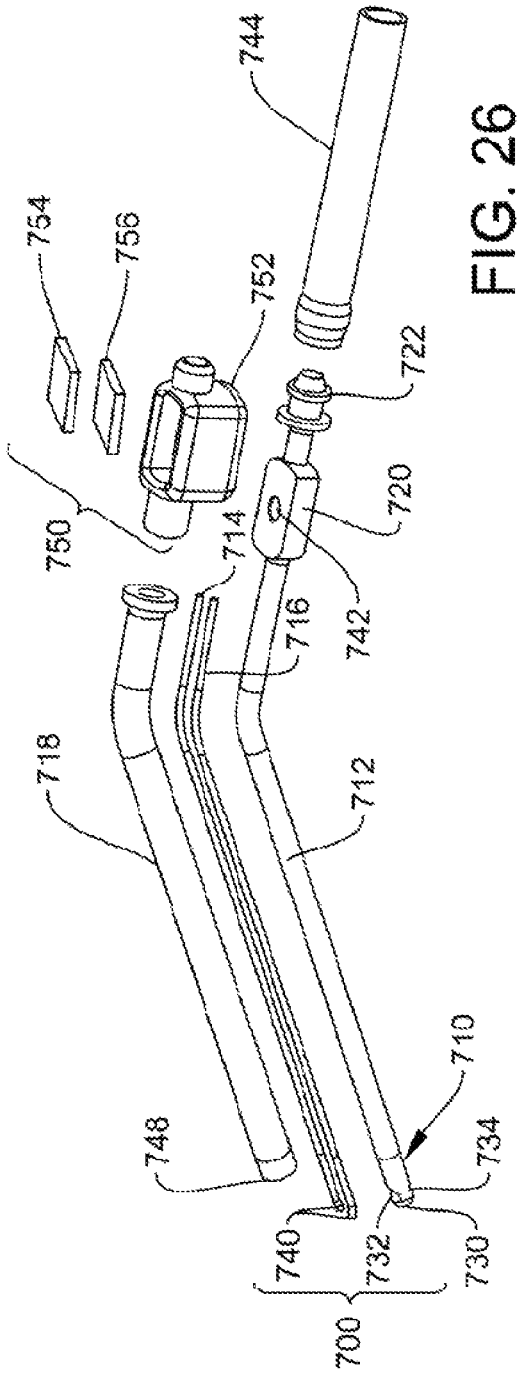
FIG. 26 is an exploded perspective view of the surgical device shown in FIG. 25.
Figures 31, 32:
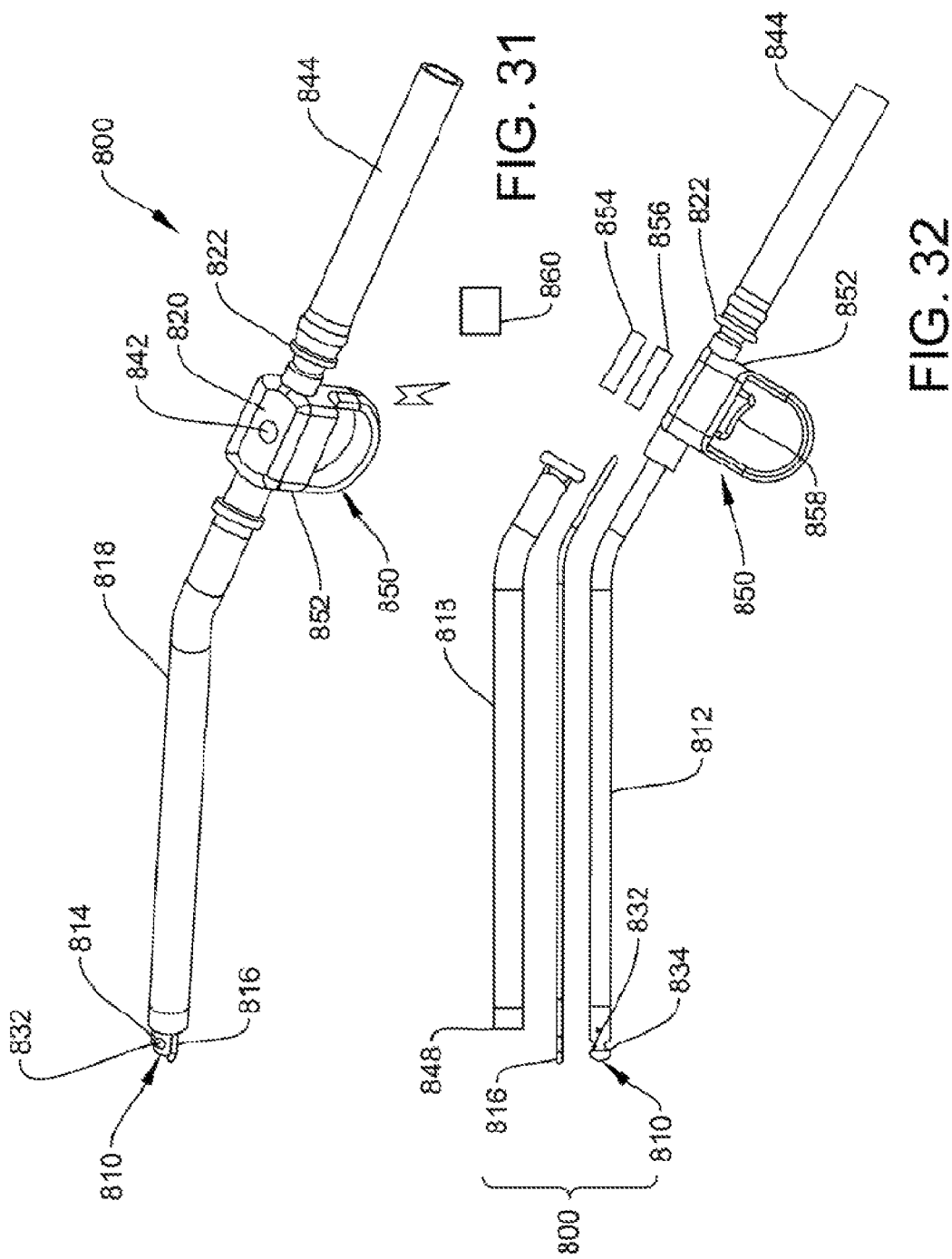
FIG. 31 is a perspective view of another example surgical device configured to mount to a suction tube and having a trigger actuator.
FIG. 32 is an exploded side view of the surgical device shown in FIG. 31.

FIG. 19 illustrates a surgical device 600 for use in treating a patient. The surgical device is disclosed with reference to FIGS. 19-36 may be particularly suited for treating a nasal cavity or other tissue internally patient. The surgical device 600 may include a suction tip 610, bipolar wires 614, 616, and an insulation cover 618. The suction tip 610, bipolar wires 614, 616, and insulation cover 618 may be combined as an assembled unit that is mounted in a separate assembly step to a suction tube 612. The suction tube 612 may be part of an existing suction device, such as, for example, the Karl Storz suction device mentioned above. The suction tube 612 may be associated with a suction control member 620, a suction tubing connector 612, and tubing extension 644. The suction control member 620 may include an opening 642 or other control device for controlling application of a suction force/flow at the distal end of the suction tube 612. The suction tube 612 is shown in FIG. 19 having a relatively straight or linear construction extending from the suction control number 620 to the distal end. Other embodiments are possible on which the suction tube has a bent or curved shape along its length, as will be described below with reference to FIGS. 20-36.

The suction tip 610 includes a distal end 630, suction ports 632, 634, and an exposed portion 636 located beyond a distal end 648 of the insulation cover 618. The exposed portion 636 is identified in FIG. 22. In at least some embodiments, the suction tip 610 is positioned within a lumen 646 of the insulation cover 618. The suction tip 610 may be permanently connected to the insulation cover 618. The bipolar wires 614, 616 may also be permanently connected to the insulation cover 618. In some embodiments, the bipolar wires 614, 616 are encapsulated within the insulation cover 618. The bipolar wires 614, 616 may be concurrently assembled during formation of the insulation cover 618 using, for example, co-molding, extrusion, or the like.

FIGS. 20-24 illustrate the surgical device 600 in use with a suction tube 612-a having a bent shape along its length. In at least some embodiments, the suction tips 610 and/or suction tube 612 may be malleable or shapeable in order to better fit into a confined space of a patient (e.g., a nasal cavity).

The proximal ends of the bipolar wires 614, 616 may be connected to a remote device 660 as shown in FIG. 20. The connection between the remote device 660 and the bipolar wires 614, 616 may be a wired connection. In some embodiments, a wireless communication may occur between the remote device 660 and the surgical device 600, in particular, the wires 614, 616 and/or a control device coupled to the wires 614, 616. In some embodiments, the remote device 660 is a foot pedal controller which is operable to control delivery of power to the wires 614, 616 to generate a cauterization zone or cauterization environment at the distal end of the surgical device 600. In other embodiments, the remote device 660 is a computing device, a computing network device, a server, or other control mechanism or system used to control one or more aspects of operation for the surgical device 600.

FIG. 21 illustrates the suction tip 610 as a separate piece from the suction tube 612. As described above, the suction tip 610 may be mounted to the insulation cover 618 (e.g., with a permanent connection). The insulation cover 618, with the suction tip 610 and bipolar wires 614, 616 mounted thereto, may be separately mounted to the suction tube 612. The suction tube 612 may be inserted into the interior 646 of the insulation cover 618 typically until contacting a proximal end of the suction tip 610. In some embodiments, an interface between the suction tube 612 and the insulation cover 618 may provide an airtight seal such that an amount of insertion of the suction tube 612 into the insulation cover 618 or whether the suction tube 612 contacts the suction tip 610 has little or no effect on the suction force applied at the suction ports 632, 634.

Referring now to FIGS. 25-30, another surgical device 700 is shown and described. The surgical device 700 may include many of the same or similar features as the surgical device 600 described above. For example, the surgical device 700 may include a suction tip 710, bipolar wires 714, 716, and an insulation cover 718 that are connected together as an assembly that is separately mounted to a suction tube 712. The suction tips 710 may include a distal end 730 and suction ports 732, 734. The distal end 730 may have a contoured or hemispherical shaped construction similar to the distal end 730 and other distal end features disclosed herein. The exposed distal ends of the bipolar wires 714, 716 may extend at least partially along the contoured distal end 730 as shown in at least FIG. 28, the distal ends of the bipolar wires 714, 716 may converge towards each other adjacent to the distal end 730. The distal most tips of the bipolar wires 714, 716 may extend distally beyond the distal end 730. Typically the suction ports 732, 734 positioned proximal of the distal most ends of the bipolar wires 714, 716.

The suction tube 712 may be associated with a suction control member 720, a suction tube connector 722, and tubing extension 744. The suction control member 720 may include a control opening 742 or other feature for controlling application of suction within the suction tube 712, particularly at the distal end of the suction tube 712.

The surgical device 700 may further include a controller assembly 750. The controller assembly 750 may include a housing 752 that is sized to receive the suction control member 720 of the suction tube 712. The housing 752 may also house a power source 754 and/or a processor 756, and other features, such as, for example, memory, electronic circuitry, a transceiver, and other electronic components. The bipolar wires 714, 716 may be connected to the electronic components (e.g., power source 754 and/or processor 756) in order to be controlled by a user. Providing the power source 754 as a battery power source may provide advantages such as, for example, eliminating wires in the operating room that may otherwise be needed to control delivery of power to the bipolar wires 714, 716, and/or provide other control features.

The controller assembly 750 and/or suction control member 720 may be in communication with a remote device 760. The remote device 760 may include, for example, a foot control pedal, a computer network or other computing system, a power source, or the like. In one embodiment, the controller assembly 750 is wirelessly connected to a foot pedal mechanism that operates to control operation of the bipolar wires 714, 716.

The insulation cover 718 may connect directly to the housing 752 of the controller assembly 750. The insulation cover 718 may provide an interface that includes, for example, an electronic connector to provide connection between the bipolar wires 714, 716 and electronic components contained in the housing 752.

The suction tube FIG. 712, including suction control members 720, may be removably positioned within housing 752. Alternatively, the housing 752 may be permanently mounted to the suction tube 712 (e.g., suction control member 720).

Another example surgical device 800 is shown and described with reference to FIGS. 31-36. The surgical device 800 may include many of the same or similar features as described above with reference to surgical devices 600, 700. Surgical device 800 may include a suction tip 810, bipolar wires 814, 816, and insulation cover 818 that are preassembled as a unit that is later mounted to a suction tube 812. The suction tip 810 may include a distal end 830 and suction ports 832, 834. The insulation cover 818 may include a distal end 848. The suction tube 812 may include a suction control member 820, a suction tubing connector 822, and a tubing extension 844. The suction control member 820 may include an opening 842 or other control featured to control application of a suction force, for example, at the distal end of the suction tube 812.

A surgical device 800 may also include a controller assembly 850 having many of the same features and functionality as the controller assembly 750 described above. The controller assembly 850 may include a housing 852, a power source 854, a processor 856 and a trigger 858. The trigger 858 may provide a finger or thumb operated mechanism for an operator to control, for example, operation of the bipolar wires 814, 816.

The controller assembly 850 may be connected together as an assembly with the suction tip 810, bipolar wires 814, 816, and insulation cover 818 (e.g., during manufacturing), and then separately connected to the suction tube 812 in another assembly step (e.g. in an operating room or physician's office). Alternatively, the controller assembly 850 may be connected to the suction tube 812, and then the suction tube 812 is inserted into the insulation cover 818, to which the suction tip 810 and bipolar wires 814, 816 have been pre-assembled together. Other embodiments, configurations, assembly methods, sub-assemblies, and capabilities may be possible using any one of the surgical devices 600, 700, 800 described herein, or in some combination with the other surgical devices disclosed with reference to FIGS. 1-18.

The signals generated by the processor and/or other electronic or computer components disclosed herein, or that may be required in order for the surgical devices disclosed herein to operate according to purpose and function of those devices as disclosed herein, may include, for example, wireless communication signals such as radio frequency, electromagnetics, local area network (LAN), wide area network (WAN), virtual private network (VPN), wireless network (using 802.11, for example), cellular network (using 3G and/or LTE, for example), and/or other signals. The network adapter may enable one or more of WWAN (GSM, CDMA, and WCDMA), WLAN (including BLUETOOTH® and Wi-Fi), WMAN (WiMAX) for mobile communications, antennas for Wireless Personal Area Network (WPAN) applications (including RFID and UWB), or any combination thereof.

One or more buses may allow data communication between one or more elements of the disclosed devices, such as a processor module, memory, I/O controller module, user interface module, network adapter, and storage adapter, or any combination thereof. One or more of the components of the devices disclosed herein, individually or collectively, may be implemented using one or more application-specific integrated circuits (ASICs) adapted to perform some or all of the applicable functions in hardware. Alternatively, the functions may be performed by one or more other processing units (or cores), on one or more integrated circuits. In other examples, other types of integrated circuits may be used such as Structured/Platform ASICs, Field Programmable Gate Arrays (FPGAs), and other Semi-Custom ICs, which may be programmed in any manner known in the art. The functions of each module may also be implemented, in whole or in part, with instructions embodied in memory formatted to be executed by one or more general and/or application-specific processors.

The memory may include random access memory (RAM), read only memory (ROM), flash memory, and/or other types. The memory may store computer-readable, computer-executable software/firmware code including instructions that, when executed, cause the processor module to perform various functions described in this disclosure. Alternatively, the software/firmware code may not be directly executable by the processor module but may cause a computer (when compiled and executed, for example) to perform functions described herein. Alternatively, the computer-readable, computer-executable software/firmware code may not be directly executable by the processor module, but may be configured to cause a computer, when compiled and executed, to perform functions described herein. The processor module may include an intelligent hardware device, for example, a central processing unit (CPU), a microcontroller, an application-specific integrated circuit (ASIC), field programmable gate array (FPGA), or any combination thereof.

In some embodiments, the memory may contain, among other things, the Basic Input-Output system (BIOS) which may control basic hardware and/or software operation such as the interaction with peripheral components or devices. For example, at least a portion of surgical device related module to implement the present systems and methods may be stored within the system memory. Applications resident with system are generally stored on and accessed via a non-transitory computer readable medium, such as a hard disk drive or other storage medium. Additionally, applications can be in the form of electronic signals modulated in accordance with the application and data communication technology when accessed via a network interface such as network adapter.

Many other devices and/or subsystems may be connected to and/or included as one or more elements of a system (for example, a personal computing device, mobile computing device, smart phone, server, internet-connected device, cell radio module, or any combination thereof). In some embodiments, all of the elements shown the figures and described herein need not be present to practice the present systems and methods. The devices and subsystems can be interconnected and operable in different ways from that shown in the figures and described herein. In some embodiments, an aspect of some operation of a system may be readily known in the art and are not discussed in detail in this application. Code to implement the present disclosure can be stored in a non-transitory computer-readable medium such as one or more of system memory or other memory. The operating system provided on I/O controller module may be a mobile device operation system, a desktop/laptop operating system, a server operating system, or another known operating system.

The I/O controller module may operate in conjunction with network adapter and/or storage adapter. The network adapter may enable an apparatus with the ability to communicate with client devices such, and/or other devices over a communication network. A network adapter may provide wired and/or wireless network connections. In some cases, the network adapter may include an Ethernet adapter or Fibre Channel adapter. A storage adapter may enable an apparatus to access one or more data storage devices such as a storage device. The one or more data storage devices may include two or more data tiers each. The storage adapter may include one or more of an Ethernet adapter, a Fibre Channel adapter, Fibre Channel Protocol (FCP) adapter, a SCSI adapter, and iSCSI protocol adapter.

Advantageously, the surgical devices disclosed herein are able to provide suction without the suction openings being obstructed, as well as cauterization using a desirable bipolar cautery system in a single device. The surgical devices disclosed herein provide a generally lower cost option for treating sinus bleeds in difficult to reach areas. The relatively low cost of the surgical devices disclosed herein may make it possible for the surgical devices to be disposable after a single use. The surgical devices disclosed herein are generally easier to manipulate and operate as part of performing a cauterization procedure within the sinuses and other difficult to reach areas of the body. The surgical devices disclosed herein may provide additional precision in treating tissue at a treatment site. The added precision may address concerns related to potential unnecessary damage that may occur when treating enflamed, bleeding, infected and other sensitive tissue and/or conditions at a treatment site. The precision and/or accuracy may be associated with the construction of the distal end portion of the surgical device, which may include malleable and steerable properties and the potential ability to customize the cauterization zone and/or intensity provided by the plurality of bipolar wires.

The detailed description set forth above in connection with the appended drawings describes examples and does not represent the only instances that may be implemented or that are within the scope of the claims. The terms "example" and "exemplary," when used in this description, mean "serving as an example, instance, or illustration," and not "preferred" or "advantageous over other examples." The detailed description includes specific details for the purpose of providing an understanding of the described techniques. These techniques, however, may be practiced without these specific details. In some instances, known structures and apparatuses are shown in block diagram form in order to avoid obscuring the concepts of the described examples.

In addition, any disclosure of components contained within other components or separate from other components should be considered exemplary because multiple other architectures may potentially be implemented to achieve the same functionality, including incorporating all, most, and/or some elements as part of one or more unitary structures and/or separate structures.

The previous description of the disclosure is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed.

The process parameters, actions, and steps described and/or illustrated in this disclosure are given by way of example only and can be varied as desired. For example, while the steps illustrated and/or described may be shown or discussed in a particular order, these steps do not necessarily need to be performed in the order illustrated or discussed. The various exemplary methods described and/or illustrated here may also omit one or more of the steps described or illustrated here or include additional steps in addition to those disclosed.

This description, for purposes of explanation, has been described with reference to specific embodiments. The illustrative discussions above, however, are not intended to be exhaustive or limit the present systems and methods to the precise forms discussed. Many modifications and variations are possible in view of the above teachings. The embodiments were chosen and described in order to explain the principles of the present systems and methods and their practical applications, to enable others skilled in the art to utilize the present systems, apparatus, and methods and various embodiments with various modifications as may be suited to the particular use contemplated.

What is claimed is:

1. A coagulation suction device, comprising:
   a hollow suction tube;
   an insulation cover having a distal end and a distal opening formed at the distal end;
   first and second bipolar wires encapsulated within the insulation cover and extending along the insulation cover to the distal end, the first and second bipolar wires extending distally beyond a distal-most surface of the insulation cover, the first and second bipolar wires each having an exposed distal end, the exposed distal ends being bent toward each other and terminating adjacent to and spaced apart from each other, wherein the hollow suction tube, the first and second bipolar wires, and the insulation cover are co-molded together, and wherein the insulation cover and the hollow suction tube are made from a polymer material; and
   a suction tip comprising a tip steering mechanism configured to change an orientation and/or direction of a distal end portion of the coagulation suction device from a location outside of a patient while the distal end portion is positioned in a body cavity of the patient.

2. The coagulation suction device of claim 1, wherein the suction tip comprises:
   a closed distal end having a radius of curvature, the closed distal end extending distally beyond the distal end of the insulation cover;
   a proximal open end positioned in the insulation cover; at least one suction opening positioned proximal of the closed distal end; wherein the suction tip is configured to be arranged in flow communication with the hollow suction tube.

3. The coagulation suction device of claim 2, wherein the insulation cover terminates proximal of the at least one suction opening.

4. The coagulation suction device of claim 2, wherein the at least one suction opening comprises at least first and second suction openings.

5. The coagulation suction device of claim 1, further comprising a trigger assembly mounted to a proximal end of the insulation cover, the trigger assembly operable to actuate the first and second bipolar wires.

6. The coagulation suction device of claim 5, wherein the trigger assembly includes a battery supply.

7. The coagulation suction device of claim 5, wherein the trigger assembly includes a wireless controller.

8. The coagulation suction device of claim 5, wherein the trigger assembly includes a housing, the housing sized to receive an on/off valve of the hollow suction tube.

9. The coagulation suction device of claim 1, further comprising wire leads electrically connected to the first and second bipolar electrodes, the wire leads being electrically connected to at least one electrode actuator.

10. A coagulation suction device, comprising:
    a suction tube;
    an insulation cover having a distal end;
    a suction tip having a portion thereof extending distally beyond the distal end of the insulation cover, a suction tip comprising a tip steering mechanism configured to change an orientation and/or direction of a distal end portion of the coagulation suction device from a location outside of a patient while the distal end portion is positioned in a body cavity of the patient, the suction tip further comprising:
       a closed distal end having a radius of curvature;
       at least one suction opening positioned proximal of the closed distal end;
    a plurality of bipolar wires encapsulated in the insulation cover, the bipolar wires having exposed distal ends extending along an outer surface of the suction tip, the bipolar wires extending toward each other at the closed distal end and following the radius of curvature of the closed distal end, wherein the suction tube, the plurality of bipolar wires, and the insulation cover are co-molded together, and wherein the insulation cover and the hollow suction tube are made from a polymer material.

11. The coagulation suction device of claim 10, further comprising a housing mounted to a proximal end of the insulation cover, the housing configured to receive a suction control member of the suction tube.

12. The coagulation suction device of claim 10, wherein the at least one suction opening includes a plurality of suction openings.

13. The coagulation suction device of claim 10, wherein the suction tip is configured to be in flow communication with the suction tube.

14. The coagulation suction device of claim 10, further comprising a trigger assembly mounted to a proximal end of the insulation cover, the trigger assembly operable to actuate the first and second bipolar wires.

15. The coagulation suction device of claim 14, wherein the trigger assembly includes a battery supply.

16. The coagulation suction device of claim 14, wherein the trigger assembly includes a wireless controller.

17. The coagulation suction device of claim 14, wherein the trigger assembly includes a finger or thumb actuated trigger member.

18. A method of operating a coagulation suction device, comprising:
providing a coagulation suction device having a suction tube, a suction tip, a plurality of bipolar wires, and an insulation cover, the suction tip mounted to a distal end of the insulation cover, the plurality of bipolar wires extending through the insulation cover and having exposed distal ends positioned adjacent to the suction tip, the exposed distal ends bending toward each other and following a contour of a closed distal surface of the suction tip, the suction tip comprising a tip steering mechanism configured to change an orientation and/or direction of a distal end portion of the coagulation suction device from a location outside of a patient while the distal end portion is positioned in a body cavity of the patient, the suction tube being in flow communication with the suction tip to provide suction flow at the suction tip, wherein the suction tube, the plurality of bipolar wires, and the insulation cover are co-molded together, and wherein the insulation cover and the hollow suction tube are made from a polymer material;
actuating the plurality of bipolar electrodes to create a cauterizing zone at the suction tip.

19. The method of claim 18, wherein the coagulation suction device further includes a battery power source mounted to the insulation cover, and actuating the plurality of bipolar electrodes includes powering the plurality of bipolar electrodes with the battery power source.

20. The method of claim 18, further comprising concurrently applying the suction flow and the cauterizing zone.

* * * * *